(12) United States Patent
Blättler et al.

(10) Patent No.: US 12,370,330 B2
(45) Date of Patent: Jul. 29, 2025

(54) DOUBLE ACTIVATION PREVENTION

(71) Applicant: PHILIP MORRIS PRODUCTS S.A., Neuchâtel (CH)

(72) Inventors: Olivier Blättler, Lamboing (CH); Onur Dayioglu, Neuchâtel (CH); Dominique Paul Gabriel Stohr, Belfaux (CH); Benjamin Crook, Bremgarten bei Bern (CH); Peter Loser, Herrenschwanden (CH); Grégoire Meylan, Marly (CH)

(73) Assignee: Philip Morris Products S.A., Neuchâtel (CH)

( * ) Notice: Subject to any disclaimer, the term of this patent is extended or adjusted under 35 U.S.C. 154(b) by 675 days.

(21) Appl. No.: 17/774,219

(22) PCT Filed: Nov. 2, 2020

(86) PCT No.: PCT/IB2020/060270
§ 371 (c)(1),
(2) Date: May 4, 2022

(87) PCT Pub. No.: WO2021/090143
PCT Pub. Date: May 14, 2021

(65) Prior Publication Data
US 2022/0347406 A1 Nov. 3, 2022

(30) Foreign Application Priority Data
Nov. 8, 2019 (EP) .................................. 19208176

(51) Int. Cl.
*A61M 15/00* (2006.01)
(52) U.S. Cl.
CPC .... *A61M 15/0021* (2014.02); *A61M 15/0035* (2014.02); *A61M 2202/064* (2013.01); *A61M 2205/273* (2013.01)

(58) Field of Classification Search
CPC .... A61M 15/00–0001; A61M 15/0021; A61M 15/0028; A61M 15/003;
(Continued)

(56) References Cited

U.S. PATENT DOCUMENTS

| 4,995,385 A | 2/1991 | Valentini et al. |
| 6,186,141 B1 * | 2/2001 | Pike ................. A61M 15/0028 128/203.12 |

(Continued)

FOREIGN PATENT DOCUMENTS

NO 20130076098 5/2013

OTHER PUBLICATIONS

European Search Report for EP 19208176.8 issued by the European Patent Office on May 11, 2020; 7 pgs.
(Continued)

*Primary Examiner* — Rachel T Sippel
(74) *Attorney, Agent, or Firm* — Mueting Raasch Group

(57) ABSTRACT

A holder for an inhaler article that includes a sleeve positioned within a housing cavity, a piercing element, and a lockout mechanism. The sleeve comprises a sleeve cavity arranged to receive the inhaler article. The sleeve is movable within the housing cavity between a first and second position. The piercing element is arranged to pierce the inhaler article received within the sleeve when the sleeve is moved from the first position to the second position. The lockout mechanism comprises a guide, a follower member coupled to the sleeve, and a retaining section. The follower member is arranged to move along the guide into the retaining section as the sleeve moves from the second position and back to the first position. The retaining section is arranged to hold the follower member when the sleeve has returned back to the first position, thus retaining the sleeve in the first position.

14 Claims, 13 Drawing Sheets

(58) Field of Classification Search
CPC .......... A61M 15/0033–0041; A61M 15/0061; A61M 15/0081; A61M 2202/064; A61M 2205/273
See application file for complete search history.

(56) References Cited

U.S. PATENT DOCUMENTS

2008/0210229 A1* 9/2008 Corbacho .......... B05B 11/1092
128/200.22
2010/0175696 A1* 7/2010 Ishizeki .............. A61M 15/003
128/203.15

OTHER PUBLICATIONS

International Search Report and Written Opinion for PCT/IB2020/060270, issued by the European Patent Office, Feb. 8, 2021; 14 pgs.
International Preliminary Report on Patentability for PCT/IB2020/060270, issued May 19, 2022; 9 pages.

* cited by examiner

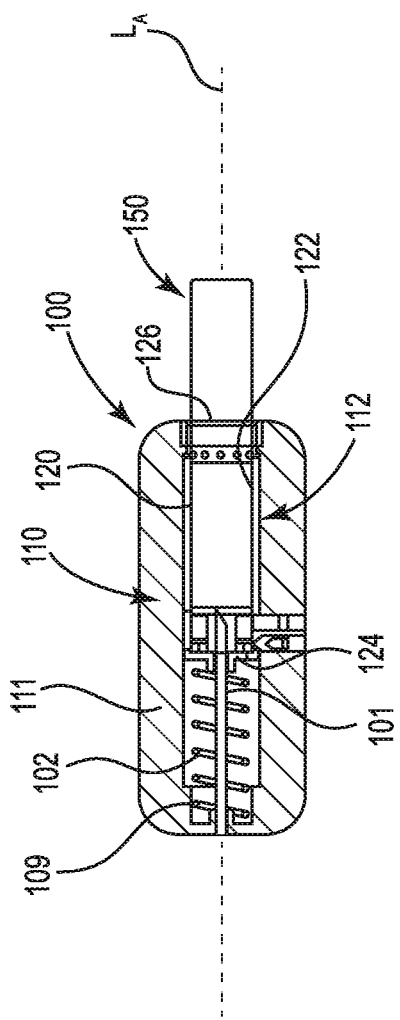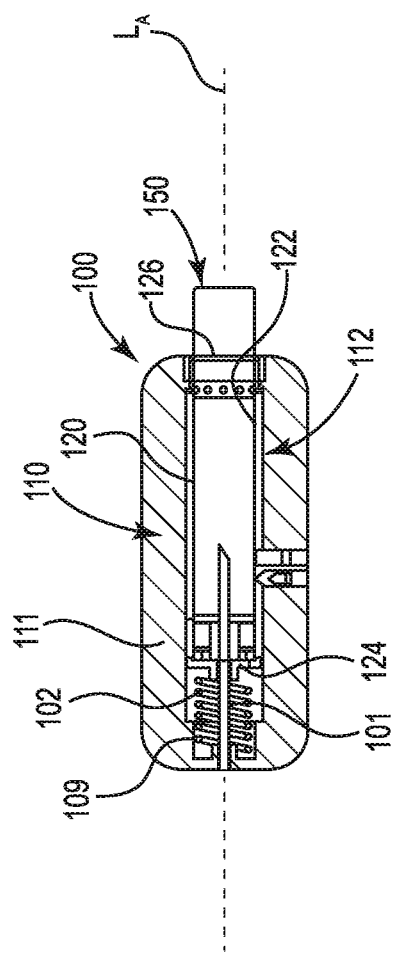

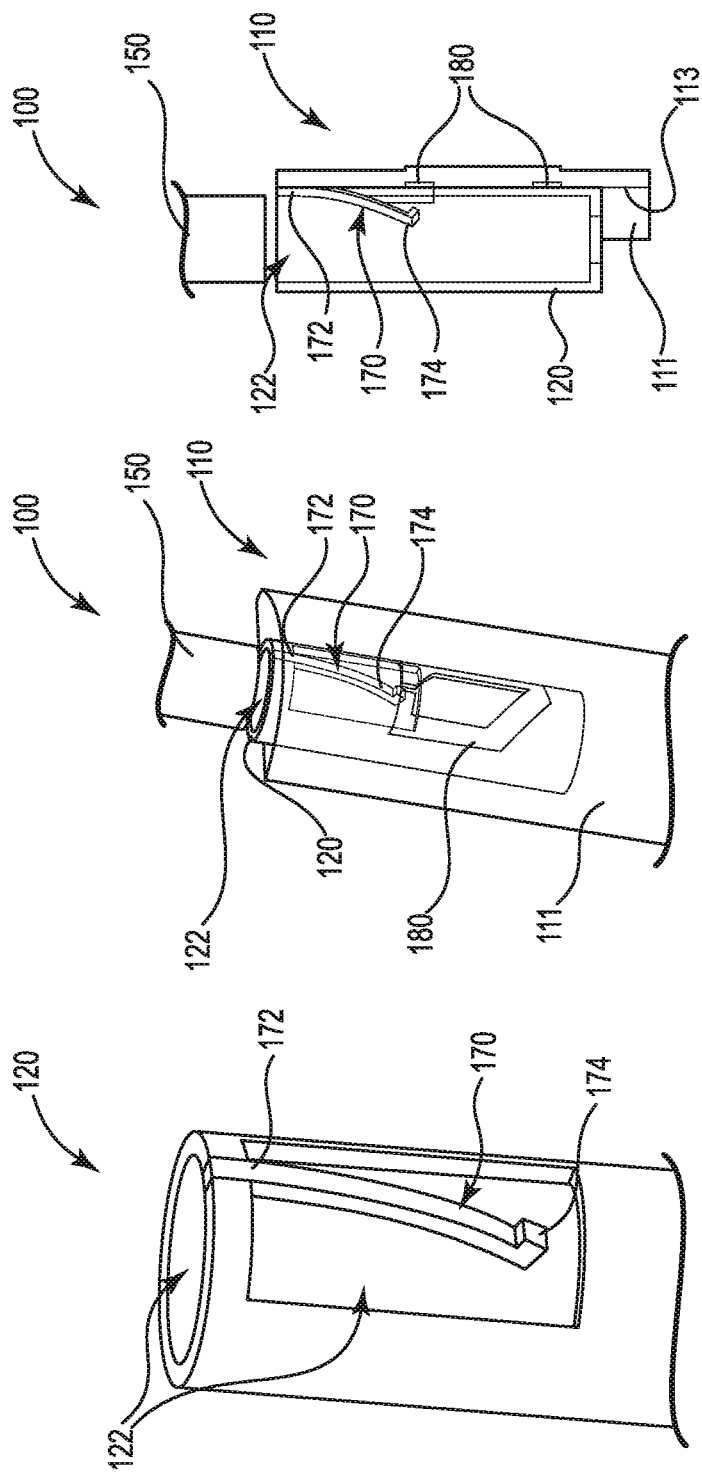

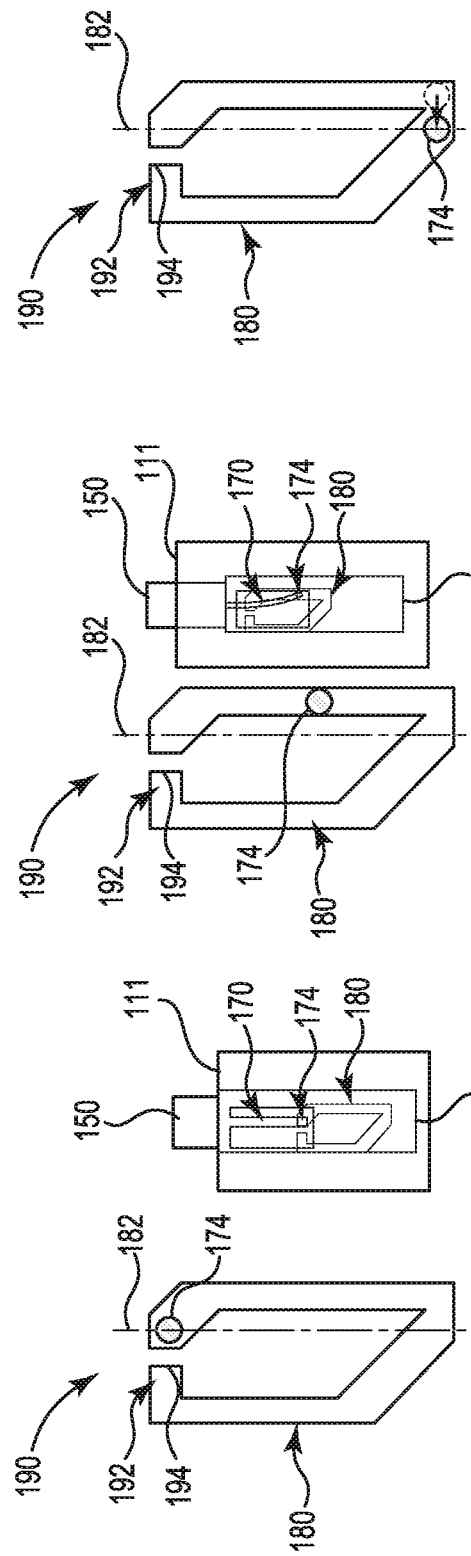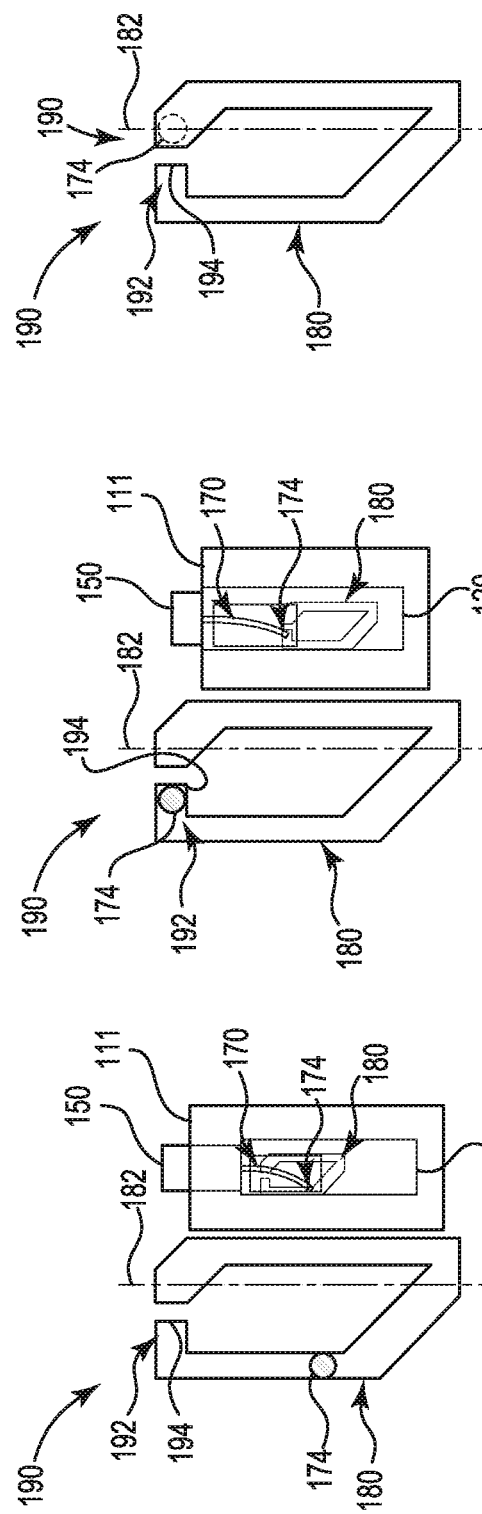

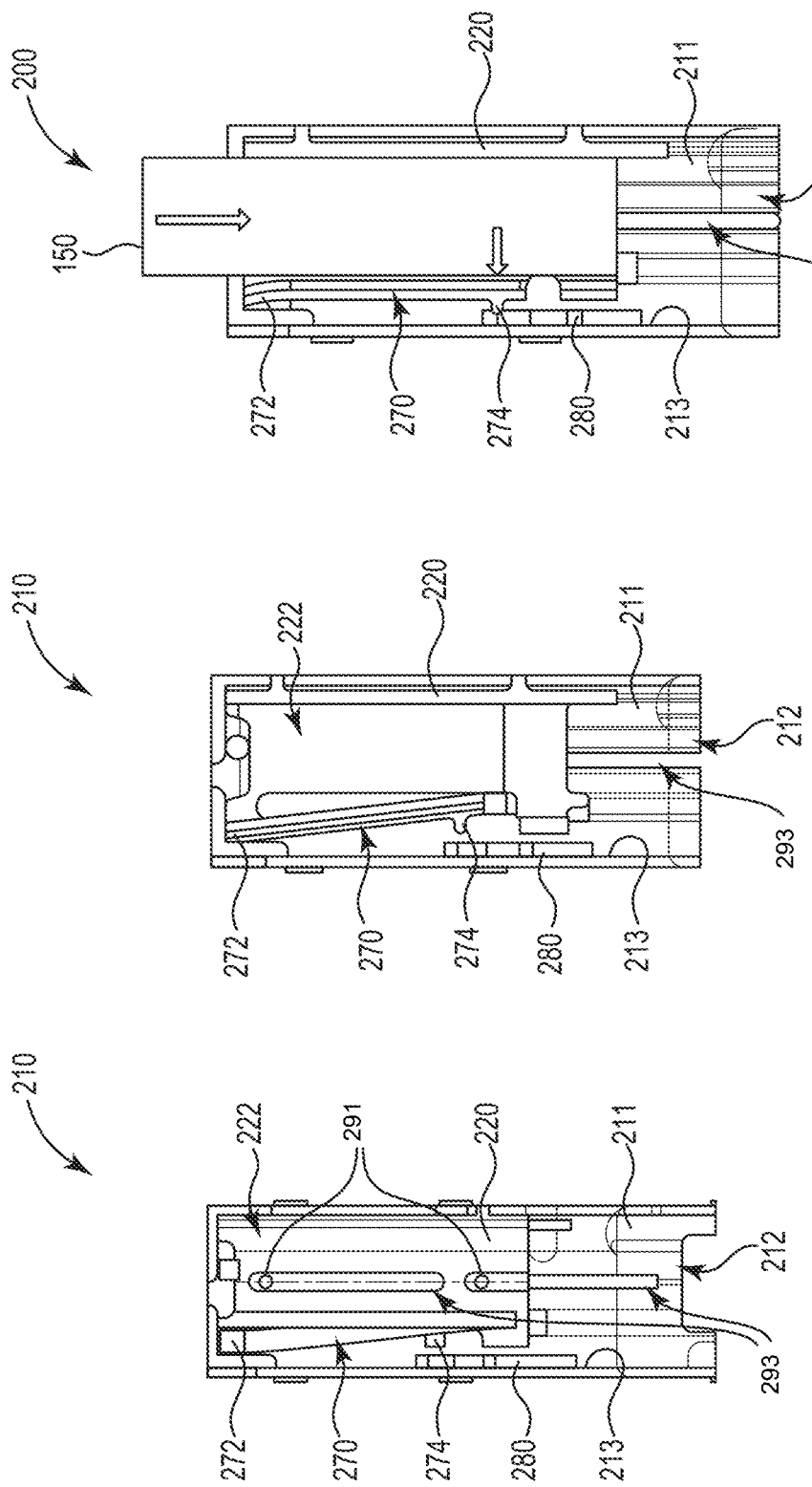

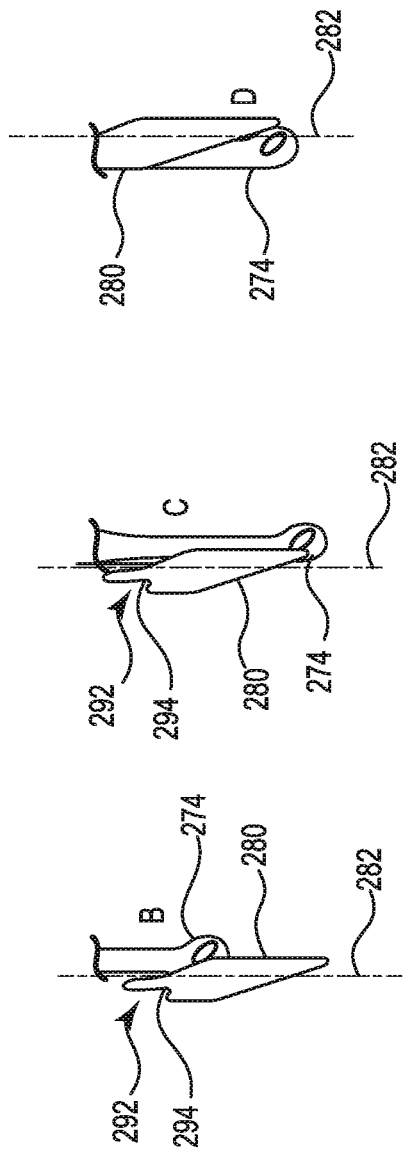
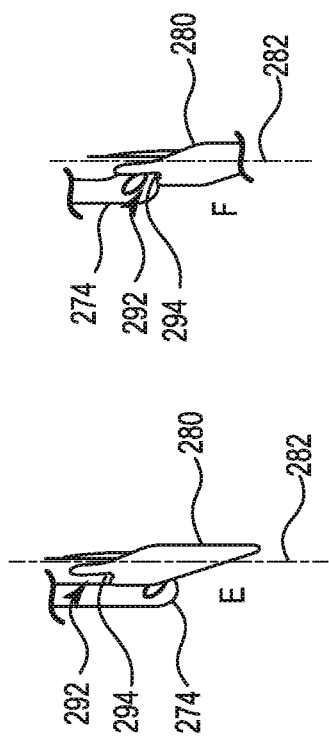
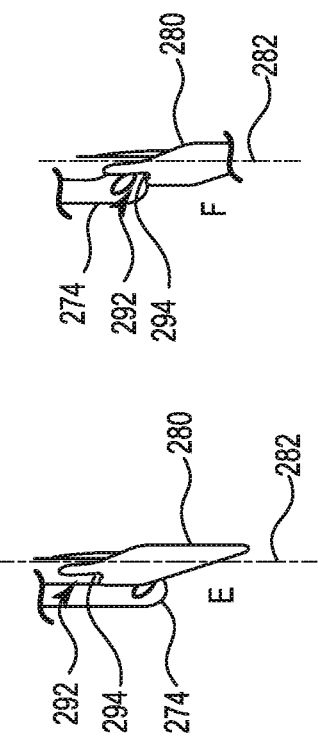
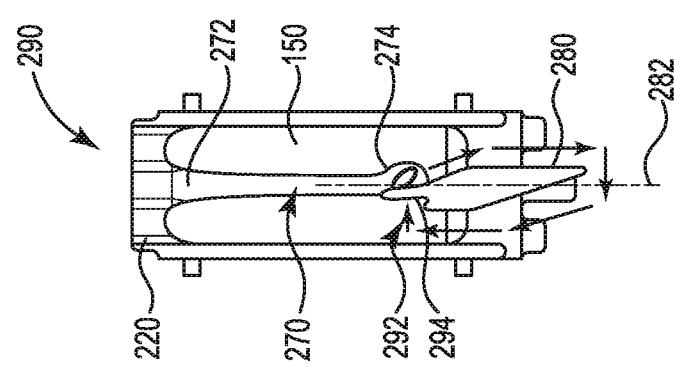

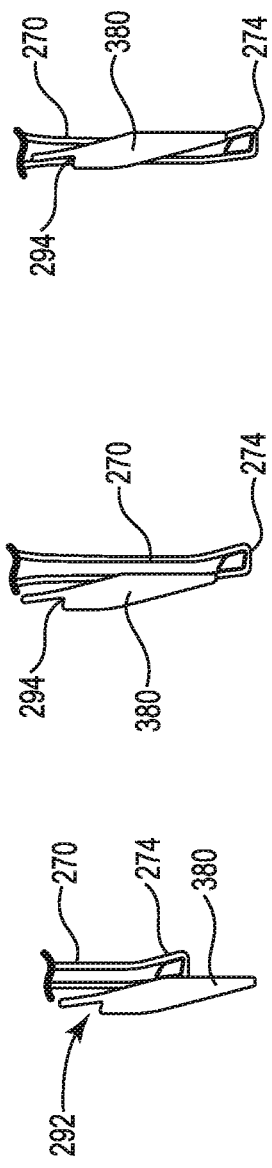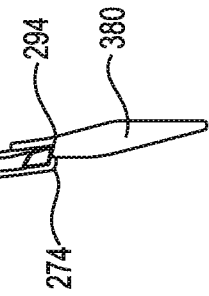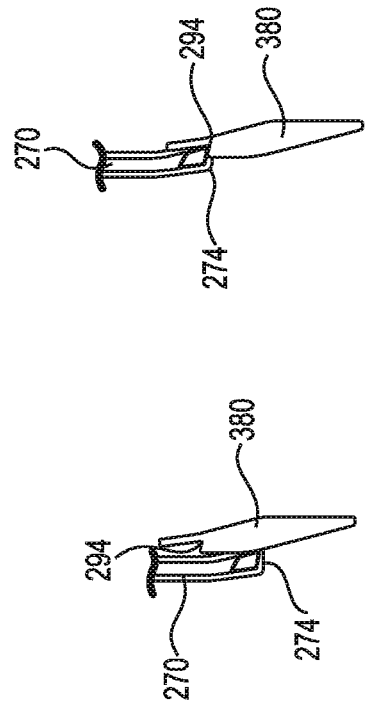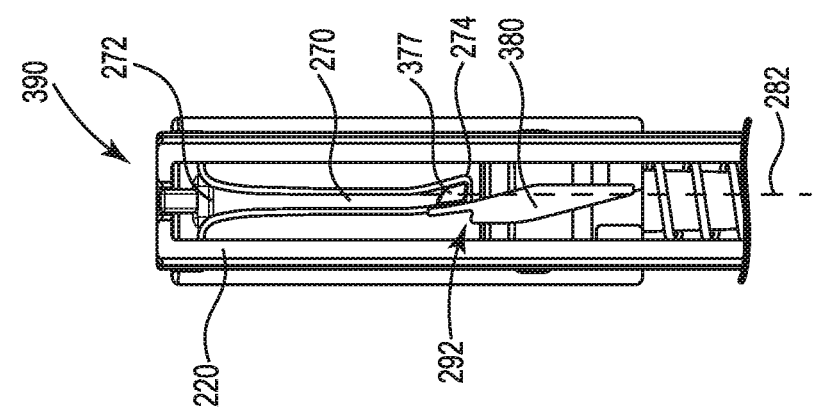

DOUBLE ACTIVATION PREVENTION

This application is the § 371 U.S. National Stage of International Application No. PCT/IB2020/060270, filed 2 Nov. 2020, which claims the benefit of European Application No. 19208176.8, filed 8 Nov. 2019, the disclosures of which are incorporated herein by reference.

The present invention relates to a holder for an inhaler article that assists in preventing activation of the inhaler article more than once.

Certain inhaler articles retain capsules containing dry powder. These capsules may be activated by piercing the capsule wall. Typically, the user typically does not receive an indication that the capsule has been pierced (or "activated"). This may lead to the user activating the capsule multiple times. Activating the capsule more than once may alter the powder delivery by increasing the size of a pierced hole or increasing the number of holes resulting in increased power delivery and a shortened user experience.

It would be desirable to provide an inhaler article that may prevent users from accidentally piercing a capsule or activating an inhaler article more than once when inhaler article is inserted into a sleeve for use.

It would be desirable to provide a holder for an inhaler article that prevents multiple activations of an inhaler article powder capsule received within the holder. It would be desirable that the inhaler system provides the user with an indication that the capsule was activated. It would also be desirable to provide an inhaler article system that is convenient to use by a consumer.

According to an aspect of the present invention, there is provided a holder for an inhaler article including a sleeve positioned within a housing cavity, a piercing element, and a lockout mechanism. The sleeve comprises a sleeve cavity arranged to receive the inhaler article. The sleeve is movable within the housing cavity between a first position and a second position. The piercing element is arranged to pierce the inhaler article received within the sleeve when the sleeve is moved from the first position to the second position. The lockout mechanism comprises a guide, a follower member coupled with the sleeve, and a retaining section. The follower member is arranged to move along the guide into the retaining section as the sleeve moves from the second position and back to the first position. The retaining section is arranged to hold the follower member when the sleeve has returned back to the first position, thus retaining the sleeve in the first position.

According to an aspect of the present invention, there is provided a holder for an inhaler article including a sleeve positioned within a housing cavity, a piercing element, and a lockout mechanism. The sleeve comprises a sleeve cavity arranged to receive the inhaler article. The sleeve is movable within the housing cavity between a first position and a second position. The piercing element is arranged to pierce the inhaler article received within the sleeve when the sleeve is moved from the first position to the second position. The lockout mechanism comprises a guide, a follower member coupled with the sleeve, and a retaining section. The follower member is arranged to move along the guide into the retaining section as the sleeve moves from the second position and back to the first position. The retaining section is arranged to hold the follower member when the sleeve has returned back to the first position, thus retaining the sleeve in the first position. The follower member is arranged to be in a neutral position in which the follower member does not interface with the guide when the inhaler article is not within the sleeve cavity.

Advantageously, incorporating a lockout mechanism in a holder for an inhaler article may prevent activation of an inhaler article more than once when the inhaler article is inserted in the sleeve for use. Additionally, incorporating a lockout mechanism that includes a guide, a follower member coupled with the sleeve, and a retaining section provides a lockout mechanism with a simple design and few moving parts and no electronics.

The follower member may be arranged to be in a neutral position in which the follower member does not interface with the guide when the inhaler article is not within the sleeve cavity. The follower member may be movable relative to the sleeve. The follower member may be arranged to interface with the inhaler article when the inhaler article is inserted into the sleeve cavity so that the inhaler article moves the follower member out of the neutral position and into contact with the guide. The follower member may extend within the sleeve cavity in the neutral position. The follower member may be flexible so that the follower member deflects outwardly away from a longitudinal axis of the sleeve into contact with the guide when the inhaler article is received in the sleeve cavity. The follower member may be biased towards the neutral position so that the follower member moves out of contact with the guide, or the retaining section when the inhaler article is removed from the sleeve, thus allowing movement of the sleeve.

Advantageously, a follower member with a neutral position within the sleeve cavity prevents the lockout mechanism from being engaged when the holder is not being used with an inhaler article. This may prevent the sleeve from locking when there is not an inhaler article in the sleeve.

The follower member and the guide may be arranged to emit an audible sound when brought into contact with one another. The guide may be arranged to move the follower member in a first lateral direction away from an initial lateral orientation as the sleeve moves from the first position to the second position. The guide may be arranged to move the follower member along a first path as the sleeve moves from the first position to the second position. The follower member may be biased towards the initial lateral orientation. The guide may be shaped so that the follower member returns to the initial lateral orientation when the sleeve is in the second position. The follower member and the guide may be arranged to emit an audible sound when the follower member returns to the initial lateral orientation.

Advantageously, a follower member and guide arranged to emit an audible sound when engaged may provide an audible indication that the lockout mechanism is engaged. Further, a follower member and a guide arranged to emit an audible sound when returning to the initial lateral orientation may provide an audible indication that an inhaler article has been moved to the appropriate position for piercing. Still further, a follower member biased to an initial lateral position may allow a guide to prevent the follower member from returning down a first path after reaching the second position.

The guide may be arranged to move the follower member in a second lateral direction by the guide as the sleeve moves from the second position to return to the first position. The second lateral direction may oppose the first lateral direction. The guide may be arranged to move the follower member along a second path as the sleeve moves from the second position to return to the first position. The retaining section may be shaped to hold the follower member within the retaining section to resist movement of the sleeve when the follower member reaches the retaining section. The retaining section may comprise at least one abutment surface arranged to resist lateral movement of the follower member.

Advantageously, a retaining section shaped to hold the follower member within the retaining section to resist movement of the sleeve when the follower member reaches the retaining section may prevent additional piercing of inhaler articles received in the sleeve. Additionally, a follower member biased to an initial lateral position may allow movement of the follower member along the guide to the retaining section that retains the form and function of the existing design while providing a mechanism that prevents accidentally piercing a capsule or activating an inhaler article more than once when the inhaler article is inserted into the sleeve for use.

The follower member may be an elongate member coupled with the sleeve. The elongate member may be integrally formed with the sleeve. The elongate member may be a component distinct from and attached to the sleeve.

Advantageously, a follower member coupled or formed integrally to the sleeve may provide a simple mechanism with few moving parts to prevent accidental piercing of a capsule or inhaler article. Additionally, a follower member that is an elongate member may allow lateral bias and movement of the follower member without requiring any complex additional features of the sleeve.

The guide may comprise a protrusion. The guide may comprise a channel. The guide may form a portion of an inner surface of the housing cavity.

Advantageously, a guide forming a portion of an inner surface of the housing cavity may provide a mechanism to prevent accidental piercing of the capsule or inhaler article without altering the outer appearance of the holder and without altering its current form and function.

The follower member may be a lever extending from a first end to a second end. The first end may be coupled to the sleeve and the second end may comprise a tip engagement feature extending from the lever. The tip engagement feature may define a pointed oval shape. The tip engagement feature may have a major longitudinal axis. The major longitudinal axis may form an angle with an axial axis of the sleeve in a range from about 30 degrees to about 75 degrees. The tip engagement feature may cooperate with the guide to produce an audible indication that the sleeve is in the second position. The follower member may have a longitudinal axis in a neutral position that is parallel with a longitudinal axis of the sleeve.

Advantageously, the follower member being a lever extending from a first end to a second end may allow lateral bias and movement of the follower member without requiring the sleeve to rotate or alter its current function. Additionally, a tip engagement feature extending from the lever may allow the follower member to engage with the guide while still allowing lateral movement of the follower member without rotation of the sleeve. Further, a tip engagement feature with a pointed oval shape may allow the follower member to move along a guide smoothly without disengaging from the guide. Still further, a tip engagement feature and guide that produce an audible indication that the sleeve is in the second position may provide an audible indication that the capsule has been pierced or the inhaler article activated.

According to another aspect of the present invention, an inhaler system comprises a holder for an inhaler article as described herein, and an inhaler article. The system further comprises a capsule disposed within a capsule cavity of the inhaler article. The capsule contains pharmaceutically active particles comprising nicotine.

Advantageously, an inhaler article may be received and activated while preventing accidental or additional activations without altering the form and function of the current design.

The pharmaceutically active particles may have a mass median aerodynamic diameter of about 5 micrometres or less, or in a range from about 0.5 micrometres to about 4 micrometres, or in a range from about 1 micrometre to about 3 micrometres.

The capsule may further contain a second population of flavour particles having a mass median aerodynamic diameter of about 20 micrometres or greater, or about 50 micrometres or greater, or in a range from about 50 to about 200 micrometres, or from about 50 to about 150 micrometres.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof.

The terms "upstream" and "downstream" refer to relative positions of elements of the holder, inhaler article and inhaler systems described in relation to the direction of inhalation air flow as it is drawn through the body of the holder, inhaler article and inhaler systems.

The terms "proximal" and "distal" are used to describe the relative positions of components, or portions of components, of the holder, inhaler article, or system. Holders or elements (such as the sleeve) forming the holder, according to the invention have a proximal end which, in use, receives an inhaler article and an opposing distal end which may be a closed end, or have an end closer to the proximal end of the holder. Inhaler articles, according to the invention have a proximal end. In use, the nicotine particles exit the proximal end of the inhaler article for delivery to a user. The inhaler article has a distal end opposing the proximal end. The proximal end of the inhaler article may also be referred to as the mouth end.

The holder for an inhaler article described herein may be combined with an inhaler article containing a capsule for activating the inhaler article by piercing the capsule, providing reliable activation of the capsule (by puncturing the capsule with the piercing element of the holder) within inhaler article, and releasing the particles contained inside the capsule and enabling the article to deliver the particles to a consumer. The holder is separate from the inhaler article, but the consumer may utilize both the inhaler article and the holder while consuming the particles released within the inhaler article. A plurality of these inhaler articles may be combined with a holder to form a system or kit. A single holder may be utilized on 10 or more, or 25 or more, or 50 or more, or 100 or more, inhaler articles to activate (puncture or pierce) a capsule contained within each inhaler article and provide reliable activation and optionally, a visual indication (marking), for each inhaler article of the activation of the inhaler article.

An inhaler system comprises an inhaler article and a holder for an inhaler article as described herein. The sleeve of the holder retains the inhaler article received in the sleeve cavity. A capsule may be disposed within the inhaler article body.

An inhaler article may comprise a body extending along an inhaler longitudinal axis from a mouthpiece end to a distal end. A capsule cavity may be defined within the body bounded downstream by a filter element and bounded upstream by a tubular element defining a central passage.

The central passage may form an air-inlet aperture extending from the distal end of the body towards the capsule cavity. A capsule may be disposed within the capsule cavity, wherein the central passage may have a smaller diameter then the capsule. Thus, the capsule may not pass through the central passage and is retained within the capsule cavity.

A holder for an inhaler article includes a sleeve positioned within a housing cavity, a piercing element, and a lockout mechanism. The sleeve comprises a sleeve cavity arranged to receive the inhaler article. The sleeve is movable within the housing cavity between a first and second position. The piercing element is arranged to pierce the inhaler article received within the sleeve when the sleeve is moved from the first position to the second position. The lockout mechanism comprises a guide, a follower member coupled to the sleeve, and a retaining section. The follower member is arranged to move along the guide into the retaining section as the sleeve moves from the second position and back to the first position. The retaining section is arranged to hold the follower member when the sleeve has returned back to the first position, thus retaining the sleeve in the first position.

The follower member may be attached to, coupled with, or integrally formed with the sleeve. The follower member may be arranged to be in a neutral position in which the follower member does not interface with the guide when the inhaler article is not within the sleeve cavity. The follower member may be arranged in the neutral position when an inhaler article is not within the sleeve cavity. In the neutral position, the follower member may extend into the sleeve cavity towards the longitudinal axis. After an inhaler article is received within the sleeve cavity, the follower member may be moved to interface with the guide. The follower member may be movable relative to the sleeve, and the follower member may be arranged to interface with the inhaler article when the inhaler article is inserted into the sleeve cavity so that the inhaler article moves the follower member out of the neutral position and into contact with the guide. When the follower member is in the neutral position, the follower member may extend within the sleeve cavity away from the guide or an inner surface of the holder. When the inhaler article is inserted into the sleeve cavity, the inhaler article may push the follower member out of the neutral position and the sleeve cavity and into contact with the guide.

The follower member may be flexible so that the follower member deflects outwardly away from a longitudinal axis of the sleeve into contact with the guide when the inhaler article is received in the sleeve cavity. The follower member may be biased towards the neutral position so that the follower member moves out of contact with the guide, or the retaining section when the inhaler article is removed from the sleeve, thus allowing movement of the sleeve. For example, if the follower member has been moved to the retaining section such that the sleeve is retained in the first position, removing the inhaler article and returning the follower member to the neutral position may allow movement of the sleeve unrestricted by the retaining section.

The follower member and the guide may be arranged to emit an audible sound when brought into contact with one another. The follower member and the guide may emit an audible sound such as a click, pop, snap, or other short sharp sound when an inhaler article is inserted into the sleeve and the follower member is brought into contact with the guide. The audible sound may provide an indication to a user that the follower member is properly seated or placed into contact with the guide.

The guide may be arranged to move the follower member in a first lateral direction away from an initial lateral orientation as the sleeve moves from the first position to the second position. The guide may be arranged to move the follower member a distance in a range of about 0.5 millimetres to about 2 millimetres in the first lateral direction as the sleeve moves from the first position to the second position. Preferably, the guide may be arranged to move the follower member a distance of about 1.2 millimetres in the first lateral direction as the sleeve moves from the first position to the second position.

The guide may be arranged to move the follower member along a first path as the sleeve moves from the first position to the second position. The follower member may be biased towards the initial lateral orientation.

The guide may be shaped so that the follower member returns to the initial lateral orientation when the sleeve is in the second position. The guide may be shaped so that the follower member cannot return up the first path when the sleeve is in the second position. The follower member and the guide may be arranged to emit an audible sound when the follower member returns to the initial lateral orientation. The follower member and the guide may emit an audible sound such as a click, pop, snap, or other short sharp sound when the sleeve is moved to the second position while the follower member is in contact with the guide. The audible sound may provide an indication to a user that the sleeve has reached the second position.

The guide may be arranged to move the follower member in a second lateral direction by the guide as the sleeve moves from the second position to return to the first position. The guide may be arranged to move the follower member a distance in a range of about 1 millimetres to about 3 millimetres in the second lateral direction as the sleeve moves from the second position to the first position. Preferably, the guide may be arranged to move the follower member a distance of about 1.8 millimetres in the second lateral direction as the sleeve moves from the second position to the first position.

The second lateral direction opposes the first lateral direction. The guide may be arranged to move the follower member along a second path as the sleeve moves from the second position to return to the first position. The follower member being returned to the initial lateral orientation at the second position may place the follower member in a position to be moved in the second lateral direction or along the second path by the guide.

The follower member may be formed of elastically deformable material. Suitable elastically deformable materials may include thermoplastic material. Suitable elastically deformable materials may include polyetheretherketone, polyamide, acetal (polyactal or polyoxymethlene), polybutylene terephthalate, styrene acrylonitrile, or other materials that can be biased and elastically deformed. Preferably, the follower member may be formed of acetal (polyactal or polyoxymethlene). Preferably, the follower member may be formed of polyetheretherketone.

The follower member may be elastically deformable or bent such that the follower member may be bent in a range of about 1.0 millimetres to about 2.0 millimetres outwardly away from the longitudinal axis and into contact with the guide when an inhaler article is received in the sleeve. Preferably, the follower member may be moved or bent about 1.5 millimetres outwardly. Additionally, the follower member may be elastically deformable or bent to accommodate movement of the follower member along the guide, in particular lateral movement in a range of about 0.5 millimetres to about 2.0 millimetres.

The follower member may be moved in the first lateral direction when moved into the retaining section. The retaining section may be offset from the initial lateral orientation in the second lateral direction. The retaining section may be shaped to hold the follower member within the retaining section to resist movement of the sleeve when the follower member reaches the retaining section. The retaining section may comprise at least one abutment surface arranged to resist lateral movement of the follower member. The abutment surface may prevent movement of the follower member back to the initial lateral orientation.

The follower member may be an elongate member coupled with the sleeve. The elongate member may be integrally formed with the sleeve. The elongate member may be a component distinct from and attached to the sleeve. The elongate member may be configured to elastically deform as it is moved by the guide.

The guide may comprise a protrusion. The protrusion may extend from an inner surface of the housing within the housing cavity. The protrusion may be coupled to the inner surface of the housing. The protrusion may be arranged to deflect the follower member and guide the follower member along a first path as the sleeve is moved from the first position to the second position. The protrusion may further be arranged to deflect and guide the follower member along a second path as the sleeve is moved from the second position to the first position.

The retaining section may comprise a retaining protrusion. The retaining protrusion may extend from an inner surface of the housing within the housing cavity. The retaining protrusion may include an abutment surface to prevent lateral movement of the follower member.

The guide may comprise a channel. The channel may extend into an inner surface of the housing within the housing cavity. The channel may be coupled to the inner surface of the housing. The channel may be configured to receive or contact a portion of the follower member within the channel. The channel may comprise a first path and a second path. The channel may be arranged to deflect the follower member and guide the follower member along the first path as the sleeve is moved from the first position to the second position. The channel may further be arranged to deflect and guide the follower member along the second path as the sleeve is moved from the second position to the first position.

The retaining section may comprise a retaining channel or recess. The retaining channel may extend from an inner surface of the housing within the housing cavity. The retaining channel may include an abutment surface to prevent lateral movement of the follower member.

The guide may form a portion of an inner surface of the housing cavity. The guide may define a protrusion of the inner surface of the housing cavity. The guide may define a channel of the inner surface of the housing cavity.

The follower member may be a lever extending from a first end to a second end, wherein the first end is coupled to the sleeve and the second end comprises a tip engagement feature extending from the lever. The lever may be configured to bend or deform from the first end to the second end as it is moved laterally by the guide. In the neutral position, the lever may be configured to bend or curve such that the second end extends into the sleeve cavity. The lever may be configured to be in the neutral position when the inhaler article is not within the sleeve cavity. The lever may be a cantilever.

The follower member may be a cantilever extending from a first end to a second end. The first end may be coupled to the sleeve. The second end may be a free end such that the second end may move independently of the first end. In other words, the second end may be bent or moved in directions different than directions of movement of the first end. The second end may be configured to engage with the guide when an inhaler article is in the sleeve cavity. The cantilever may be configured to bend or deform from the first end to the second end as it is moved by the inhaler article or the guide.

The tip engagement feature may define a pointed oval shape. The tip engagement feature may have a major longitudinal axis. The major longitudinal axis may form an angle with an axial axis of the sleeve in a range from about 30 degrees to about 75 degrees. Preferably, the major longitudinal axis may form an angle with an axial axis of the sleeve of about 55 degrees. The tip engagement feature may have an engagement feature distance defining a distance between the axial axis of the sleeve and an edge of the tip engagement feature. The engagement feature distance may be in a range of about 0.5 millimetres to about 2 millimetres. Preferably, the engagement feature distance is about 1 millimetre. The tip engagement feature may cooperate with the guide to produce an audible indication that the sleeve is in the second position.

The follower member may have a longitudinal axis in a neutral position that is parallel with a longitudinal axis of the sleeve. The sleeve may be configured to receive and be disposed about a distal end region of an inhaler article. The sleeve may have a base surface for contacting the distal end of an inhaler article. The base surface may define a distal end of the sleeve and oppose an open proximal end of the sleeve. The sleeve may extend from the distal end to the open proximal end. The sleeve may retain an inhaler article via interference fit.

The sleeve may include an aperture at the distal end of the sleeve and the piercing element may extend thorough the aperture. The distal end of the inhaler article may contact the base surface of the sleeve and urge the sleeve to travel toward the piercing element. The sleeve may be co-axial with the piercing element. The sleeve may align the inhaler article so that the piercing element reliably activates capsule within the inhaler article. The sleeve may also mechanically hold the piercing element and support the piercing element to prevent or mitigate deflection of the piercing element.

The sleeve may define a first air inlet zone comprising at least one air aperture through the sleeve. The first air inlet zone may include two or more, three or more, four or more, or from about 1 to about 10 air apertures, or from about 3 to about 9 air apertures. The first air inlet zone is proximate to a proximal end of the sleeve. The first air inlet zone is configured to allow air to flow from an inside of the sleeve to an airflow channel formed between the sleeve and the housing inner surface.

The sleeve may comprise a second air inlet zone comprising at least one air aperture through the sleeve. The second air inlet zone may include two or more, three or more, four or more, or from about 1 to about 10 air apertures, or from about 3 to about 9 air apertures. The second air inlet zone is proximate to a distal end of the sleeve. The second air inlet zone is configured to allow air to flow from the airflow channel to an inside of the sleeve.

In some embodiments, the potion of the inner cavity between the first air inlet zone and the second air inlet zone may have a reduced diameter. In these embodiments, the air (inhalation air) is unable to pass from the proximal end of the sleeve to the distal end of the sleeve between the sleeve and the inhalation article. In these embodiments, the provision of a first and second air inlet zone advantageously allows air to enter the open end of the holder and pass to the distal end of an inhaler article while still allowing the article to be securely retained in the sleeve. Thus, the inhaler article may be consumed by a user while the inhaler article is contained within the holder.

The holder may include a retaining ring element fixed to the open proximal end of the housing. The retaining ring element retains the sleeve within the inhaler article cavity. The retaining ring has a thickness sufficient to stop or retain the movement of the sleeve within the inhaler article cavity of the holder.

The holder may include a spring element configured to bias the sleeve between a relaxed (first) and compressed (second) position towards the open proximal end of the housing. The spring element may be contained within the inhaler article cavity of the holder and be compressed as the movable sleeve and inhaler article move toward the piercing element. The spring element may be between the sleeve and distal end of the housing and contacts the sleeve and distal end of the housing. The spring element may be disposed about the piercing element. The spring element may be co-axial with the piercing element. The spring element may be a conical spring.

The spring element may be fixed to the distal end of the holder. The spring element may be fixed to the distal end of the sleeve. The spring element may be fixed to both the distal end of the holder and the distal end of the sleeve. The spring element may be a conical spring. The conical spring advantageously may provide a low-profile design so that it may provide a more flexible design and smaller overall compression thickness. The provision of a conical spring may also advantageously reduce the likelihood that the spring will buckle when compressed compared to a cylindrical spring.

The spring element biases the inhaler article out of engagement with and away from the piercing element once the piercing element activates the inhaler article. The spring element may be disposed about the piercing element. The spring element may be coaxial with the piercing element. The piercing element may extend beyond the spring element when the spring element is in a relaxed position. The piercing element may extend beyond the spring element when the spring element is in a compressed position. The piercing element may extend beyond the spring element when the spring element is in both the relaxed position and the compressed position. The piercing element may extend beyond the spring element when the sleeve compresses the spring element.

Recessing the piercing element into the housing protects the piercing element from coming into contact with surfaces not intended to be received within the piercing element. Recessing the piercing element into the housing may also protect the piercing element from being damaged or modified by surfaces not intended to be received within the piercing element.

The piercing element length may be any suitable length relative to the housing length. For example, the piercing element length may be about 25% to about 60%, or about 30% to about 50%, of the housing length. A distal end of the piercing element may be fixed to the distal end adjacent to or at the distal end of the housing. The piercing element entire length may be coextensive within the housing length.

The piercing element is formed of a rigid material. The rigid material is sufficiently rigid to pierce, puncture or activate a capsule contained within the inhaler article. The piercing element may be formed of a metal. The piercing element may be formed of stainless steel, such as 316 stainless steel, for example. The piercing element may be formed of a polymeric material. The piercing element may be formed of a fibre-reinforced polymeric material.

The housing may be formed of any rigid material. The housing may be formed of a polymeric material. Polymeric materials useful for forming the housing include polycarbonate, polypropylene, polyethylene, nylon, acrylonitrile butadiene styrene, styrene acrylonitrile, polyacrylate, polystyrene, PBT polyester, PET polyester, polyoxymethylene, polysulfone, polyethersulfone, polyethereetherketone, or liquid crystal polymer, for example. Polyproplyene, polyethylene or co-polymers thereof are preferred materials for forming the housing.

The inhaler article may be received into the holder such that the inhaler article outer surface and the holder housing outer surface are concentric. The piercing element longitudinal axis may be coaxial with the housing longitudinal axis, and the inhaler longitudinal axis, when the inhaler article is received within the holder. At least about 50%, or at least about 75% of the housing length may be coextensive with the inhaler length, when the inhaler article is received within the holder.

The holder may be formed by insertion moulding techniques. The piercing element may first be formed by moulding, for example, and then the housing may be moulded around the piercing element bonding to the piercing element. The piercing element may be a metal piercing element, the housing may be moulded around the metal piercing element fixing the metal piercing element to the housing. A metal piercing element may include protrusions or recesses at the distal end of the piercing element to increase surface area of the distal end of the piercing element and improve fixation within the housing moulded material.

An inhaler article air channel may extend through the end cap or endpiece element of the inhaler article to provide airflow through the inhaler article. The air channel supplying airflow to the capsule cavity may be configured to receive or induce a swirling air flow pattern within the capsule cavity of the inhaler body. The air channel configuration may induce rotational air flow or swirling air flow as the air flows through the air channel and through the capsule cavity. Air flow through the inhaler article may enter the inhaler article at the distal end of the inhaler article and moves along the longitudinal axis of the inhaler article to the mouthpiece end. Air flow through the inhaler article may enter the inhaler article along the inhaler body upstream or along the capsule cavity and move along the longitudinal axis of the inhaler article to the mouthpiece end.

The inhaler body may resemble a smoking article or cigarette in size and shape. The inhaler body may have an elongated body extending along the longitudinal axis of the inhaler article. The inhaler body may have a substantially uniform outer diameter along the length of the elongated body. The inhaler body may have a circular cross-section that may be uniform along the length of the elongated body. The inhaler body may have an outer diameter in a range from about 6 mm to about 10 mm, or from about 7 mm to about 10 mm, or about 7 mm to about 9 mm, or about 7 mm to about 8 mm or about 7.2 mm. The inhaler body may have a length (along the longitudinal axis) in a range from about 40 mm to about 80 mm, or from about 40 mm to about 70 mm, or about 40 mm to about 50 mm, or about 45 mm.

The inhaler article may have an open distal end or upstream-most end defined by a tubular element defining a central passage. The open central passage may define a cylindrical open aperture extending from the capsule cavity to the open distal end or upstream-most end of the inhaler article. The open tubular element defining an open central passage may have a length in a range from about 3 mm to about 12 mm, or from about 3 mm to about 7 mm or about 4 mm to about 6 mm, or about 5 mm.

The open tubular element defining an open central passage may be formed of a cellulose material. The open tubular element defining an open central passage may be formed of a cellulose acetate material. Preferably the open tubular element is formed of a biodegradable material. The open tubular element defining an open central passage may have a thickness in a range from about 0.5 mm to about 1.5 mm, or about 0.5 mm to about 1 mm.

The filter element located downstream of the capsule cavity may extend from the capsule cavity to the mouthpiece end of the inhaler article. The filter element may have a length in a range from about 10 mm to about 30 mm, preferably from about 15 mm to about 25 mm and more preferably from about 20 mm to about 22 mm.

The capsule cavity may define a cylindrical space configured to contain a capsule (the capsule may have an obround shape or a circular cross-section, for example). The capsule cavity may have a substantially uniform or uniform diameter along the length of the capsule cavity. The capsule cavity may have a fixed cavity length. The capsule cavity has a cavity inner diameter, orthogonal to the longitudinal axis, and the capsule has a capsule outer diameter. The capsule cavity may be sized to contain an obround capsule. The capsule cavity may have a substantially cylindrical or cylindrical cross-section along the length of the capsule cavity. The capsule cavity may have a uniform inner diameter. The capsule may have an outer diameter that is about 80% to about 95% of the inner diameter of the capsule cavity. The configuration of the capsule cavity relative to the capsule may promote limited movement of the capsule during activation or piercing of the capsule.

The capsule cavity may be defined by an open tubular element. The open tubular element may be joined between and in abutting alignment with the open tubular element forming the distal end of the inhaler article and the filter element. These elements may be joined with a wrapper. The open tubular element defining the capsule cavity may be formed of a biodegradable material, such as cardboard or paperboard.

The configuration of the capsule cavity relative to the capsule may promote the capsule to rotate with stability within the capsule cavity. The longitudinal axis of the capsule may rotate with stability co-axially with the longitudinal axis of the inhaler body during inhalation. The configuration of the capsule cavity relative to the capsule may promote the capsule to rotate with some shaking within the capsule cavity.

Stable rotation refers to the longitudinal axis of the inhaler body being substantially parallel or co-axial with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" or inhalations by a consumer.

The capsule may be sealed within the inhaler article prior to consumption. The inhaler article may be contained within a sealed or airtight container or bag. The inhaler article may include one or more peelable or removable seal layers to cover the one or more air inlet channels or the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler. The capsule may be formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 1 to size 4 capsule, or a size 3 capsule.

The separate holder, as described herein, forms a single aperture through the capsule received in the capsule cavity.

The capsule may contain nicotine particles comprising nicotine (also referred to as "nicotine powder" or "nicotine particles") and optionally particles comprising flavour (also referred to as "flavour particles). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder, or from about 25 mg to about 100 mg of a dry powder.

The dry powder or powder system may have at least about 40%, or at least about 60%, or at least about 80%, by weight of the powder system comprised in nicotine particles having a particle size of about 5 micrometers or less, or in a range from about 1 micrometer to about 5 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free-flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include a population of flavour particles. The flavour particles may have any useful size distribution for inhalation delivery selectively into the mouth or buccal cavity of a user.

The powder system may have at least about 40%, or at least about 60%, or at least about 80%, by weight of the population of flavour particles of the powder system comprised in particles having a particle size of about 20 micrometres or greater. The powder system may have at least about 40% or at least about 60%, or at least about 80%, by weight of the population of flavour particles of the powder system comprised in particles having a particle size of about 50 micrometres or greater. The powder system may have at least about 40% or at least about 60%, or at least about 80%, by weight of the population of flavour particles of the powder system comprised in particles having a particle size in a range from about 50 micrometer to about 150 micrometres.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus, agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free-flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler system may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

According to an aspect of the present invention, there is provided a holder for an inhaler article. The holder may include a sleeve positioned within a housing cavity. The holder may include a piercing element. The holder may include a lockout mechanism. The sleeve may comprise a sleeve cavity arranged to receive the inhaler article. The sleeve may be movable within the housing cavity between a first position and a second position. The piercing element may be arranged to pierce the inhaler article received within the sleeve when the sleeve is moved from the first position to the second position. The lockout mechanism may comprise a guide. The lockout mechanism may comprise a follower member coupled with the sleeve. The lockout mechanism may comprise a retaining section. The follower member may be arranged to move along the guide into the retaining section as the sleeve moves from the second position and back to the first position. The retaining section may be arranged to hold the follower member when the sleeve has returned back to the first position, thus retaining the sleeve in the first position.

Below there is provided a non-exhaustive numbered list of non-limiting examples. Any one or more of the features of these examples may be combined with any other one or more features of another example, embodiment, or aspect described herein.

1: A holder for an inhaler article, the holder comprising a sleeve positioned within a housing cavity, wherein the sleeve comprises a sleeve cavity arranged to receive the inhaler article and the sleeve is movable within the housing cavity between a first position and a second position; a piercing element arranged to pierce the inhaler article received within the sleeve when the sleeve is moved from the first position to the second position; and a lockout mechanism comprising a guide, a follower member coupled with the sleeve, and a retaining section; wherein the follower member is arranged to move along the guide into the retaining section as the sleeve moves from the second position and back to the first position; and wherein the retaining section is arranged to hold the follower member when the sleeve has returned back to the first position, thus retaining the sleeve in the first position.

2: The holder according to example 1 wherein the follower member is arranged to be in a neutral position in which the follower member does not interface with the guide when the inhaler article is not within the sleeve cavity.

3: The holder according to example 2 wherein the follower member is movable relative to the sleeve, and the follower member is arranged to interface with the inhaler article when the inhaler article is inserted into the sleeve cavity so that the inhaler article moves the follower member out of the neutral position and into contact with the guide.

4: The holder according to example 2 or example 3 wherein the follower member extends within the sleeve cavity in the neutral position.

5: The holder according to example 4 wherein the follower member is flexible so that the follower member deflects outwardly away from a longitudinal axis of the sleeve into contact with the guide when the inhaler article is received in the sleeve cavity.

6: The holder according to any one of examples 2 to 5 wherein the follower member is biased towards the neutral position so that the follower member moves out of contact with the guide, or the retaining section when the inhaler article is removed from the sleeve.

7: The holder according to any one of the preceding examples wherein the follower member and the guide are arranged to emit an audible sound when brought into contact with one another.

8: The holder according to any one of the preceding examples wherein the guide is arranged to move the follower member in a first lateral direction away from an initial lateral orientation as the sleeve moves from the first position to the second position.

9: The holder according to example 8 wherein the guide is arranged to move the follower member along a first path as the sleeve moves from the first position to the second position.

10: The holder according to example 8 or example 9 wherein the follower member is biased towards the initial lateral orientation; and wherein the guide is shaped so that the follower member returns to the initial lateral orientation when the sleeve is in the second position.

11: The holder according to example 10 wherein the follower member and the guide are arranged to emit an audible sound when the follower member returns to the initial lateral orientation.

12: The holder according to any one of examples 8 to 11 wherein the guide is arranged to move the follower member in a second lateral direction by the guide as the sleeve moves from the second position to return to the first position.

13: The holder according to example 12 wherein the second lateral direction opposes the first lateral direction.

14: The holder according to example 12 or example 13 wherein the guide is arranged to move the follower member along a second path as the sleeve moves from the second position to return to the first position.

15: The holder according to any one of the preceding examples wherein the retaining section is shaped to hold the follower member within the retaining section to resist movement of the sleeve when the follower member reaches the retaining section.

16: The holder according to example 15 wherein the retaining section comprises at least one abutment surface arranged to resist lateral movement of the follower member.

17: The holder according to any one of the preceding examples wherein the follower member is an elongate member coupled with the sleeve.

18: The holder according to example 17 wherein the elongate member is integrally formed with the sleeve.

19: The holder according to example 17 wherein the elongate member is a component distinct from and attached to the sleeve.

20: The holder according to any one of the preceding examples wherein the guide comprises a protrusion.

21: The holder according to any one of examples 1 to 19 wherein the guide comprises a channel.

22: The holder according to any one of the preceding examples wherein the guide forms a portion of an inner surface of the housing cavity.

23: The holder according to any one of the preceding examples wherein the follower member is a lever extending from a first end to a second end, wherein the first end is coupled to the sleeve and the second end comprises a tip engagement feature extending from the lever.

24: The holder according to example 23 wherein the tip engagement feature defines a pointed oval shape.

25: The holder according to example 23 or example 24 wherein the tip engagement feature has a major longitudinal axis, the major longitudinal axis forms an angle with an axial axis of the sleeve in a range from about 30 degrees to about 75 degrees.

26: The holder according to any one of examples 23 to 25 wherein the tip engagement feature cooperates with the guide to produce an audible indication that the sleeve is in the second position.

27: The holder according to any one of the preceding examples wherein the follower member has a longitudinal axis in a neutral position that is parallel with a longitudinal axis of the sleeve.

28: An inhaler system comprising the holder according to any one of the preceding examples and an inhaler article, the system further comprising a capsule disposed within a capsule cavity of the inhaler article, wherein the capsule contains pharmaceutically active particles comprising nicotine.

29: The inhaler system according to example 28 wherein the pharmaceutically active particles have a mass median aerodynamic diameter of about 5 micrometres or less, or in a range from about 0.5 micrometres to about 4 micrometres, or in a range from about 1 micrometres to about 3 micrometres.

30: The inhaler system according to example 29 wherein the capsule further contains a second population of flavour particles having a mass median aerodynamic diameter of about 20 micrometres or greater, or about 50 micrometres or greater, or in a range from about 50 to about 200 micrometres, or from about 50 to about 150 micrometres.

The invention will now be further described with reference to the figures in which:

FIGS. 2A and 2B are cross-sectional schematic diagrams of the illustrative inhaler system of FIG. 1;

FIG. 4A is a partial isometric view of an illustrative sleeve;

FIG. 4B is a partial isometric view of an illustrative holder of an inhaler article;

FIG. 4C is cross-sectional schematic diagram of an illustrative holder of FIG. 4B;

FIGS. 6A-6F are schematic diagrams of an illustrative guide;

FIG. 7A is a cross-sectional schematic diagram of an illustrative holder;

FIG. 7B is another cross-sectional schematic diagram of an illustrative holder of FIG. 7A;

FIG. 7C is a cross-sectional schematic diagram of an illustrative inhaler system;

FIGS. 8A-8F are cross-sectional schematic diagrams of an illustrative lockout mechanism;

FIGS. 11A-11F are cross-sectional schematic diagrams of another illustrative lockout mechanism;

FIG. 113A is a cross-sectional schematic diagram of an illustrative sleeve.

Figure 1:
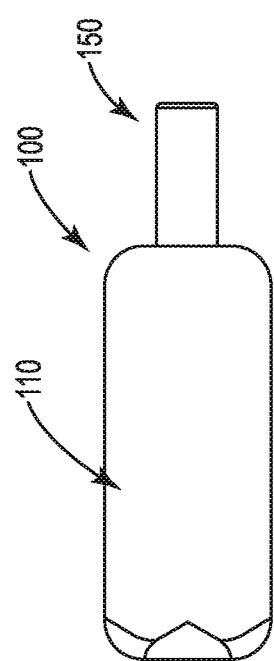
FIG. 1 is a top view of an illustrative inhaler system.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 3:
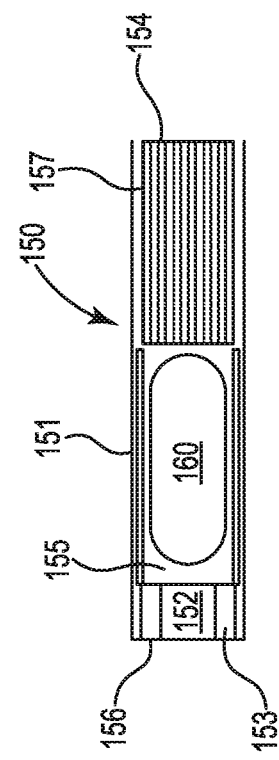
FIG. 3 is a cross-sectional schematic diagram of an illustrative inhaler article.

FIG. 1 is a perspective view of an illustrative inhaler system 100. FIG. 2A is a cross-sectional schematic diagram of an illustrative inhaler system 100 of FIG. 1 with a sleeve 120 in a first position. FIG. 2A is a cross-sectional schematic diagram of the illustrative inhaler system 100 of FIG. 1 with the sleeve in a first position and FIG. 2B is a cross-sectional schematic diagram of the illustrative inhaler system 100 with the sleeve 120 in a second position. FIG. 3 is a cross-sectional schematic diagram of an illustrative inhaler article 150 of FIGS. 1, 2A, and 2B.

The inhaler system 100 includes an inhaler article 150 and a separate holder 110. The inhaler article 150 is received within the holder 110 to activate or pierce a capsule 160 disposed within the inhaler article 150. The inhaler article 150 may remain in the holder 110 during use by the consumer. The holder 110 and the inhaler article 150 may be configured to provide swirling inhalation airflow through the received inhaler article 150.

The inhaler system 100 includes the inhaler article 150 and the holder 110. The inhaler article 150 includes a body 151 extending along an inhaler longitudinal axis $L_A$ from a mouthpiece end 154 to a distal end 156. The capsule 160 is disposed within the inhaler article body 151. The holder 110 includes a movable sleeve 120 that retains the inhaler article 150 received in a sleeve cavity 122.

The holder 110 for the inhaler article 150 includes a housing 111 comprising a housing cavity 112 for receiving an inhaler article 150 and the sleeve 120 is configured to retain an inhaler article 150 within the housing cavity 112. The sleeve 120 extends from an open proximal end 126 to an opposing distal end 124. The sleeve 120 defines a sleeve cavity 122 and is movable within the housing cavity 112 along the longitudinal axis $L_A$ of the housing 111 between a first and second position.

In these examples, the holder 110 includes a piercing element 101 fixed to and extending from a housing inner surface 109. The piercing element 101 is configured to extend through the second opposing end 124 of the sleeve 120 and into the sleeve cavity 122 along a longitudinal axis of the housing 111. The holder 110 includes a spring element 102 configured to bias the sleeve 120 away from the piercing element 101 or toward the open end of the holder 110 in the first position.

The inhaler article 150 comprises the body 151 that extends along an inhaler longitudinal axis $L_A$ from the mouthpiece end 154 to the distal end 156. A capsule cavity 155 is disposed within the body 151 and is bounded downstream by a filter element 157 and bounded upstream by a tubular element 153 defining a central passage 152. The central passage 152 forms an air-inlet aperture extending from the distal end 156 of the body towards the capsule cavity 155. A capsule 160 is disposed within the capsule cavity 155. The central passage 152 has a smaller diameter then the capsule 160.

The housing 110 may have an overall longitudinal length in a range from about 40 mm to about 60 mm. The sleeve 120 may have an overall longitudinal length in a range from about 15 mm to about 30 mm. The spring element 102 may have an overall longitudinal length in a range from about 15 mm to about 30 mm. The sleeve 120 may travel or be movable an overall longitudinal distance in a range from about 15 mm to about 30 mm between a first and second position. The spring 102 may compress an overall longitudinal distance in a range from about 15 mm to about 30 mm.

In the first position, the piercing element 101 does not extend within the capsule cavity 155 so that the capsule 160 is not pierced when the inhaler article 150 is positioned in the sleeve cavity 122 when the sleeve 120 is in the first position. In the second position, the piercing element 101 does extend within the capsule cavity 155 so that the capsule 160 is pierced when the inhaler article 150 is positioned in the sleeve cavity 122 when the sleeve 120 is in the second position. The first position may be referred to as an "relaxed position", and the second position may be referred to as a "compressed position".

In one embodiment, the inhaler article 150 has a longitudinal length of about 45 mm, and the holder 110 has a longitudinal length of about 50 mm to about 55 mm. Once received in the holder 110 (and the sleeve 120 and spring element 102 in the first or relaxed position), the inhaler article 150 has about 50% of its longitudinal length received within the holder 110 and about 50% of its longitudinal length extending from the holder 110. In this embodiment, a consumer may urge the inhaler article 150 onto the piercing element, compressing the spring element 102 and moving the sleeve to the second position, puncturing the capsule 160 to activate the capsule 160. In the second or compressed position, less than about 20% of the inhaler article 150 longitudinal length extends from the holder 110 or about 1 mm to about 5 mm of the inhaler article 150 longitudinal length extends from the holder 110. The linear or longitudinal distance between the relaxed and compressed position may be from about 15 mm to about 25 mm, or about 20 mm.

Figure 5C:
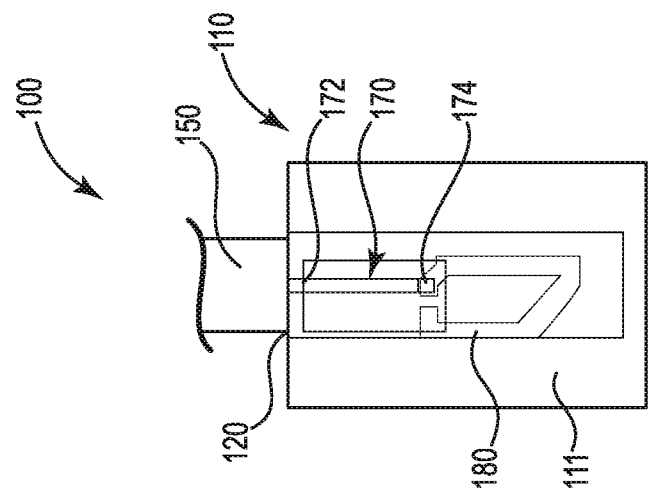
FIG. 5C is a partial perspective view of an illustrative holder of FIGS. 5A and 5B.
Figure 5B:
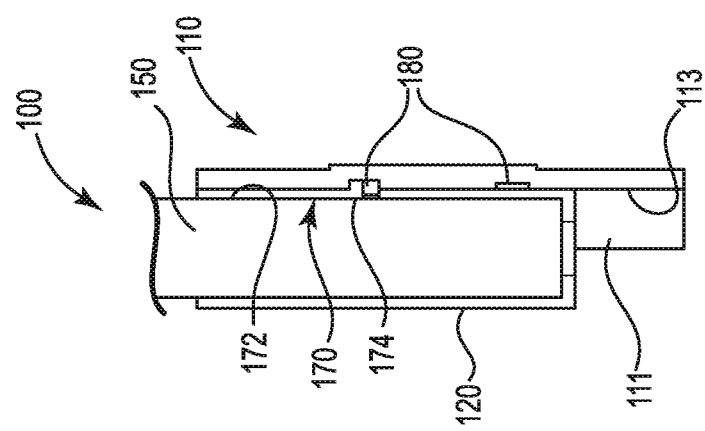
FIG. 5B is a cross-sectional schematic diagram of an illustrative holder of FIG. 5A.
Figure 5A:
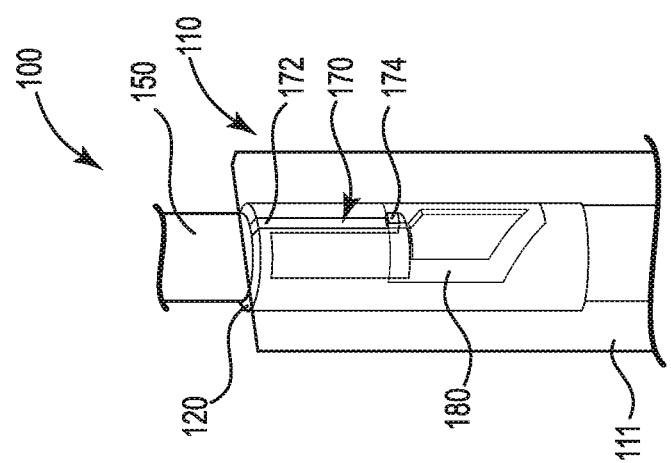
FIG. 5A is a partial isometric view of an illustrative holder of an inhaler article.

FIG. 4A is a partial isometric view of an illustrative sleeve 120 and a follower member 170. FIG. 4B is a partial isometric view of an illustrative inhaler system 100 including the sleeve 120 and follower member 170 of FIG. 4A. FIG. 4C is a cross-sectional schematic diagram of an illustrative inhaler system 100 of FIG. 4B. FIGS. 4A-4C showing the sleeve 120 prior to insertion of the inhaler article 150. FIG. 5A is a partial isometric view of an illustrative inhaler system 100 of FIGS. 4B and 4C. FIG. 5B is a cross-sectional schematic diagram of an illustrative inhaler system 100 of FIG. 5A. FIG. 5C is a partial perspective view of an illustrative inhaler system 100 of FIGS. 5A and 5B. FIGS. 5A-5C showing the inhaler article fully inserted into the sleeve 120 and in contact with the follower member 170 thereby moving the follower member 170 into the guide 180. FIGS. 5A-5C showing the sleeve 120 in the first position.

The follower member 170 extends from a first end 172 to a second end 174. The follower member 170 is coupled to the sleeve 120 at the first end 172. The second end 174 may be referred to as the free end. In this example, the follower member 170 is integrally formed with the sleeve 120. However, the follower member 170 could be a separate component that is connected to the sleeve 120 about a hinge, for instance.

FIG. 4A shows the follower member 170 in a neutral position in which the follower member 170 extends axially into the sleeve cavity 122. The follower member 170 may be biased towards assuming the neutral position such that the follower member 170 may be in the neutral position when the inhaler article 150 has not been received in sleeve cavity 122. The follower member 170 may not be engaged in a guide 180 when in the neutral position. In this example, the guide 180 is a channel or groove in an inner surface 113 of the housing 111.

The follower member 170 is arranged to interface with the inhaler article 150 when the inhaler article is received in the sleeve cavity 122. The inhaler article 150 may move or bias the follower member 170 out of the neutral position and into contact with the guide 180 on the inner surface 113 of the housing 111. The follower member 170 is flexible or elastic so that the follower member 170 deflects outwardly away from a longitudinal axis of the sleeve and into contact with the guide 180 on the inner surface 113 of the housing 111.

FIGS. 6A-6F are schematic diagrams of an illustrative lockout mechanism 190 of an illustrative holder 110 of FIGS. 1, 2, 4B-4C, and 5A-5C. FIG. 6A is a schematic diagram of the illustrative lockout mechanism 190 when the sleeve 120 is at a first position before activation of an inhaler article 150. FIG. 6B is a schematic diagram of an illustrative lockout mechanism 190 as the sleeve 120 is being moved from the first position to the second position. FIG. 6C is a schematic diagram of an illustrative lockout mechanism 190 when the sleeve 120 is at the second position. FIG. 6D is a schematic diagram of an illustrative lockout mechanism 190 when the sleeve 120 is being moved from the second position back to the first position. FIG. 6E is a schematic diagram of an illustrative lockout mechanism 190 when the sleeve 120 has been returned to the first position. FIG. 6F is a schematic diagram of an illustrative lockout mechanism 190 when an inhaler article 150 has been removed from the sleeve 120.

At FIG. 6A an inhaler article 150 has been received in the sleeve 120 and the follower member 170 has been moved into contact with the guide 180 and resides at an initial lateral orientation 182. The guide 180 is arranged to emit an audible indication that the follower member 170 has been moved into contact with the guide 180. At FIG. 6B the guide 180 moves the follower member 170 (specifically the second end 174) along a first path as the sleeve 120 moves from the first position to the second position. As the sleeve 120 is moved from the first position to the second position the guide 180 moves the follower member 170 in a first lateral direction away from the initial lateral orientation 182.

At FIG. 6C the sleeve 120 is at the second position and the guide 180 is shaped so that the follower member 170 returns to the initial lateral orientation 182. The guide 180 is arranged to emit an audible sound when the follower member 170 returns to the initial lateral orientation 182. The audible sound indicates to the consumer that the capsule has been activated.

At FIG. 6D the guide 180 moves the follower member 170 in a second lateral direction as the sleeve 120 moves from the second position to return to the first position. The second lateral direction opposes the first lateral direction. The guide 180 is arranged to move the follower member 170 along a second path as the sleeve 120 moves from the second position to return to the first position.

At FIG. 6E the follower member has returned to the first position and is now held in the retaining section 192. The retaining section 192 is shaped to hold the follower member 170 within the retaining section 192 to resist movement of the sleeve 120 when the follower member 170 reaches the retaining section 192. The retaining section 192 includes an abutment surface 194 arranged to resist lateral movement of the follower member 170. Accordingly, the abutment surface 194 prevents the follower member 170 from returning to the initial lateral orientation 182 which prevents movement of the sleeve 120 after activation of the inhaler article 150.

At FIG. 6F the inhaler article 150 has been removed from the sleeve 120 and the follower member 170 has moved out of contact with the guide, thus allowing movement of the sleeve 120. Furthermore, the follower member 170 has returned to the initial lateral orientation 182 such that receiving an inhaler article, such as inhaler article 150, will place the lockout mechanism 190 in the arrangement depicted in FIG. 6A and the process can be repeated with additional inhaler articles.

In this example, the guide 180 is a channel. As shown, the guide 180 is formed on an inner surface 113 of the housing 111. In this example, the second end 174 of the follower member 170 comprises a tip engagement feature. The second end 174 of the follower member 170 is arranged to contact the guide 180 when an inhaler article is received in the sleeve 120. The second end 174 is arranged to move along paths of the guide 180 as the sleeve 120 is moved between the first and second positions while the second end 174 is in contact with the guide 180.

FIG. 7A is a cross-sectional schematic diagram of an illustrative holder 210 without the inhaler article 150 inserted. FIG. 7B is a cross-sectional schematic diagram of an illustrative holder 210 of FIG. 7A without the inhaler article 150 inserted. FIG. 7C is a cross-sectional schematic diagram of an illustrative inhaler system 200 including an illustrative holder 210 of FIGS. 7A and 7B with the inhaler article 150 inserted and pushing the follower member 270 into contact with a guide 280.

The follower member 270 extends from a first end 272 to a second end 274. The follower member 270 is coupled to the sleeve 220 at the first end 272 and extend to the second or free end 274. In this example, the follower member 270 is integrally formed with the sleeve 220. The follower member 270 extends axially into a sleeve cavity 222 when in a neutral position. The follower member 270 is biased in the neutral position such that the follower member 270 is in the neutral position when the inhaler article 150 has not been received in sleeve cavity 222. The follower member 270 is not engaged in the guide 280 when in the neutral position. As shown, the guide 280 is a protrusion in an inner surface 213 of the housing 211.

The holder 210 includes a sleeve 220 and follower member 270. In this example, the holder 210 further includes elongated slots 293 extending along a longitudinal length of the holder 210. The sleeve 220 further includes alignment pins 291 extending from an outer surface of the sleeve 220. The alignment pins 291 are configured to mate with the elongated slots 293. This provision of the elongate slots and the corresponding alignment pins 291 advantageously guides the longitudinal movement of the sleeve 220 in the housing cavity 212. In particular, the one or more alignment pins 291 prevent rotation of the sleeve 220 in the housing cavity 212.

The follower member 270 is arranged to interface with the inhaler article 150 when the inhaler article is received in the sleeve cavity 222. The inhaler article 150 moves the follower member 270 out of the neutral position and into contact with the guide 280. The follower member 270 is flexible so that the follower member 270 deflects outwardly away from a longitudinal axis of the sleeve and into contact with the guide 280.

FIG. 8A-8F are schematic diagrams of an illustrative lockout mechanism 290 of an illustrative holder 210 of FIGS. 7A-7C. FIG. 8A is a schematic diagram of an illustrative lockout mechanism 290 when a sleeve 220 is at a first position before activation of an inhaler article 150. FIG. 8B is a schematic diagram of an illustrative lockout mechanism 290 as the sleeve 220 is being moved from the first position to the second position. FIG. 8C is a schematic diagram of an illustrative lockout mechanism 290 when the sleeve 220 is moved to a position just before the second position. FIG. 8D is a schematic diagram of an illustrative lockout mechanism 290 when the sleeve 220 is moved to the second position. FIG. 8E is a schematic diagram of an illustrative lockout mechanism 290 when the sleeve 220 is being moved from the second position back to the first position. FIG. 8F is a schematic diagram of an illustrative lockout mechanism 290 when the sleeve 220 has been returned to the first position.

At FIG. 8A an inhaler article 150 has been received in the sleeve 220 and the follower member 270 has been moved into contact with the guide 280 and resides at an initial lateral orientation 282. Follower member 270 is fixed to the sleeve 220 at the first end 272 and extends to a free or second end 274. The guide 280 may be arranged to emit an audible indication that the follower member 270 has been moved into contact with the guide 280.

At FIG. 8B the guide 280 moves the follower member second end 274 along a first path, or edge of the guide 280 as the sleeve 220 moves from the first position to the second position. As the sleeve 220 is moved from the first position to the second position the guide 280 moves the follower member second end 274 in a first lateral direction away from the initial lateral orientation 282.

At FIG. 8C the sleeve 220 is moved to a position just before the second position and the follower member second end 274 is prevented from moving to the initial lateral orientation 282 by the guide 280. At FIG. 8D the sleeve 220 is at the second position and the guide 280 is shaped so that the follower member second end 274 returns to the initial lateral orientation 282. The guide 280 may be arranged to emit an audible sound when the follower member second end 274 returns to the initial lateral orientation 282. The audible sound is produced by the follower member second end 274 flicking past or off of the guide 280. The audible sound indicates to the consumer that the capsule has been activated.

At FIG. 8E the guide 280 moves the follower member second end 274 in a second lateral direction as the sleeve 220 moves from the second position to return to the first position. The second lateral direction opposes the first lateral direction. The guide 280 is arranged to move the follower member second end 274 along a second path as the sleeve 220 moves from the second position to return to the first position.

At FIG. 8F the follower member has returned to the first position and is now held in the retaining section 292. The retaining section 292 is shaped to hold the follower member second end 274 within the retaining section 292 to resist movement of the sleeve 220 when the follower member second end 274 reaches the retaining section 292. The retaining section 292 includes an abutment surface 294 arranged to resist lateral movement of the follower member second end 274. Accordingly, the abutment surface 294 prevents the follower member second end 274 from returning to the initial lateral orientation 282 which prevents movement of the sleeve 220 after activation of the inhaler article 150.

After the inhaler article 150 is been removed from the sleeve 220, the follower member second end 274 moves out of contact with the guide, thus allowing movement of the sleeve 220. Furthermore, the follower member 270 returns to the initial lateral orientation 282 such that receiving an inhaler article, such as inhaler article 150, will place the lockout mechanism 290 in the arrangement depicted in FIG. 8A and the process can be repeated with additional inhaler articles.

In this example, the guide 280 comprises a protrusion. For instance, the guide 280 is formed on an inner surface of the holder 210, or the guide 280 is a separate component attached to the inner surface of the holder 210. In this example, the second end 274 of the follower member 270 comprises a tip engagement feature. As shown, the tip engagement feature defines a pointed oval shape. This shape may reduce the chance of the tip engagement feature catching on the surface of the guide 280 while facilitating being held in the retaining section 292. The second end 274 of the follower member 270 is arranged to contact the guide 280 when an inhaler article is received in the sleeve 220. The second end 274 is arranged to move along a perimeter of the guide 280 as the sleeve 220 is moved between the first and second positions while the second end 274 is in contact with the guide 280.

Figure 9C:
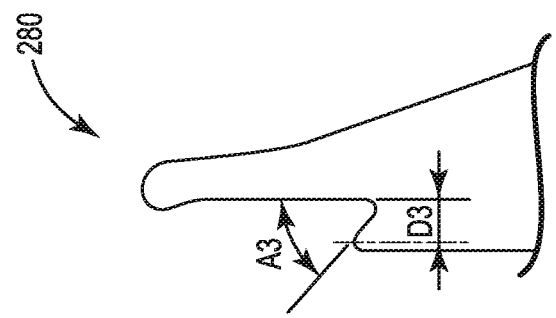
FIGS. 9A-9C are schematic diagrams of an illustrative guide.
Figure 9B:
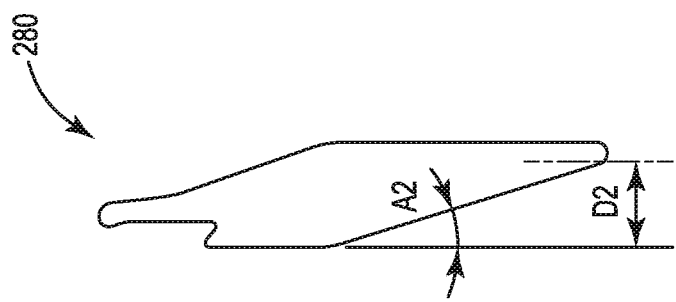
Figure 9A:
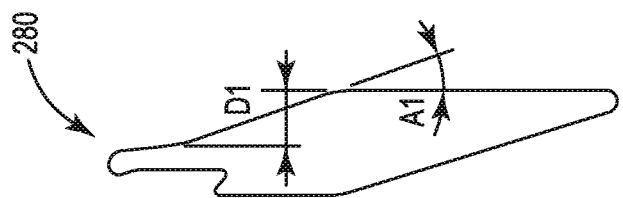

FIG. 9A is a schematic diagram of an illustrative guide 280 first, second, third and fourth portions, which may be referred to as "edges". The first portion is the first portion of the guide 280 with which the follower member 270 comes into contact when the follower member 270 first contacts the guide 280. The second portion is the portion of the guide 280 with which the follower member 270 comes into contact when the follower member 270 has left contact with the first portion of the guide 280. The third portion is the portion of the guide 280 with which the follower member 270 comes into contact when the follower member 270 has left contact with the second portion of the guide 280. The fourth portion is the portion of the guide 280 with which the follower member 270 comes into contact when the follower member 270 has left contact with the third portion of the guide 280, before coming into contact with the retaining section.

FIG. 9A shows a follower member tensioning rate angle A1 and a follower member tensioning rate distance D1. The tensioning rate angle A1 is the angle between the first and second portions of the guide 280. The follower member tensioning rate distance D1 is the lateral distance travelled by the follower member 270 along the first portion.

FIG. 9B is a schematic diagram of the illustrative guide 280 of FIG. 9A including follower member tensioning rate angle A2 and follower member tensioning rate distance D2. The tensioning rate angle A2 is the angle between the third and fourth portions of the guide 280. The follower member tensioning rate distance D2 is the lateral distance travelled by the follower member 270 along the third portion.

FIG. 9C is a schematic diagram of the illustrative guide 280 of FIGS. 9A and 9B including follower member tensioning rate angle A3 and follower member tensioning rate distance D3. The follower member tensioning rate angle A3 is the angle between the fourth portion and the retaining section surface. The follower member tensioning rate distance D3 is the lateral distance travelled by the follower member 270 along the retaining section surface.

The activation angle A1 is in a range of about 10 degrees to about 30 degrees. Preferably, the activation angle A1 is about 20 degrees. The activation distance D1 is in a range of about 0.5 millimetres to about 2 millimetres. Preferably, the activation distance D1 is about 1.2 millimetres.

The return angle A2 is in a range of about 10 degrees to about 30 degrees. Preferably, the return angle A2 is about 18 degrees. The return distance D2 is in a range of about 1 millimetres to about 3 millimetres. Preferably, the return distance D2 is about 1.8 millimetres.

The retainer angle A3 is in a range of about 0 degrees to about 90 degrees. Preferably, the retainer angle A3 is about 53 degrees. The retainer distance D3 is in a range of about 0.2 millimetres to about 1 millimetre. Preferably, the retainer distance D3 is about 0.45 millimetres.

Figure 10B:
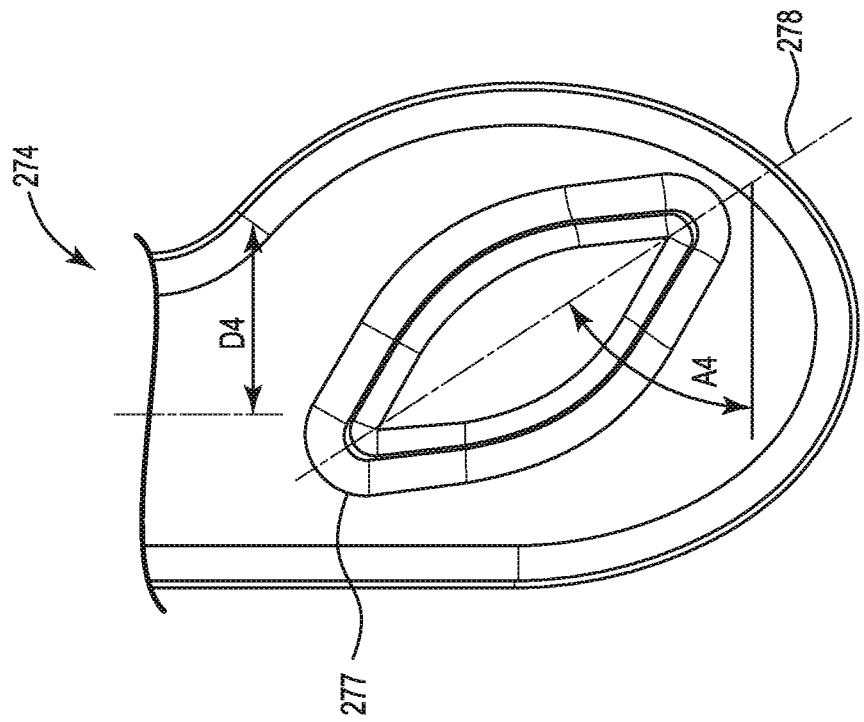
FIG. 10B is a perspective view of an illustrative follower member.
Figure 10A:
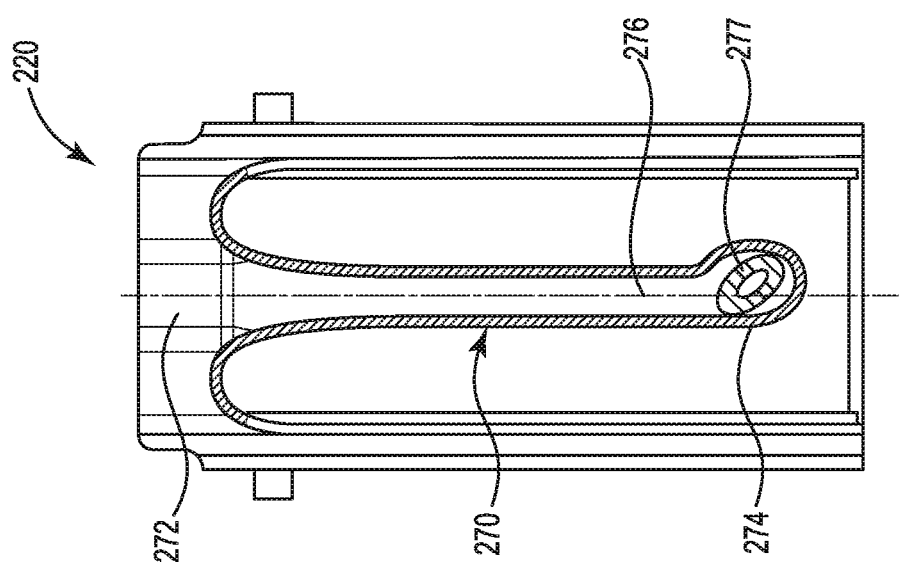
FIG. 10A is a cross-sectional schematic diagram of an illustrative sleeve.

FIG. 10A is a cross-sectional schematic diagram of an illustrative sleeve 220. FIG. 10B is a perspective view of a second end 274 of the follower member 270 of FIG. 10A.

The follower member 270 extends between a first end 272 and a second end 274. The follower member 270 extends along a sleeve axis 276. The first end 272 may be coupled to or formed integrally with the sleeve 220. The second end 274 of the follower member 270 comprises a tip engagement feature 277. As shown, the tip engagement feature 277 has a pointed oval shape. The pointed oval shape has a major longitudinal axis 278. An engagement feature distance D4 from an edge of the tip engagement feature 277 to the sleeve axis 276 may be in a range from about 0.5 millimetres to about 2 millimetres. Preferably, the engagement feature distance D4 may be about 1 millimetres. An engagement feature angle A4 is the angle at which the length of the engagement feature 277 is offset from an axis perpendicular to the length of the follower member 270 may be in a range of about 30 degrees to about 75 degrees. Preferably, the engagement feature angle A4 may be about 56 degrees.

FIG. 11A-11F are schematic diagrams of an illustrative lockout mechanism 390 of an illustrative holder 210 of FIGS. 7A-7C. FIG. 11A is a schematic diagram of an illustrative lockout mechanism 390 when a sleeve 220 is at a first position before activation of an inhaler article 150 (see FIG. 7C). FIG. 11B is a schematic diagram of an illustrative lockout mechanism 390 as the sleeve 220 is being moved from the first position to the second position. FIG. 11C is a schematic diagram of an illustrative lockout mechanism 390 when the sleeve 220 is moved to a position just before the second position. FIG. 11D is a schematic diagram of an illustrative lockout mechanism 390 when the sleeve 220 is moved to the second position. FIG. 11E is a schematic diagram of an illustrative lockout mechanism 390 when the sleeve 220 is being moved from the second position back to the first position. FIG. 11F is a schematic diagram of an illustrative lockout mechanism 390 when the sleeve 220 has been returned to the first position.

At FIG. 11A an inhaler article 150 (see FIG. 7C) has been received in the sleeve 220 and the follower member 270 has been moved into contact with the guide 380 and resides at an initial lateral orientation 282. Follower member 270 is fixed to the sleeve 220 at the first end 272 and extends to a free or second end 274. The guide 380 may be arranged to emit an audible indication that the follower member 270 has been moved into contact with the guide 380.

At FIG. 11B the guide 380 moves or deflects the follower member second end 274 along a first path, or edge of the guide 380 as the sleeve 220 moves from the first position to the second position. As the sleeve 220 is moved from the first position to the second position the guide 380 moves the follower member second end 274 in a first lateral direction away from the initial lateral orientation 282.

At FIG. 11C the sleeve 220 is moved to a position just before the second position and the follower member second end 274 is prevented from moving to the initial lateral orientation 282 by the guide 380. At FIG. 11D the sleeve 220 is at the second position and the guide 380 is shaped so that the follower member second end 274 returns to the initial lateral orientation 282. The guide 380 may be arranged to emit an audible sound when the follower member second end 274 returns to the initial lateral orientation 282. The audible sound is produced by the follower member second end 274 flicking past or off of the guide 380. The audible sound indicates to the consumer that the capsule has been activated.

At FIG. 11E the guide 380 moves or deflects the follower member second end 274 in a second lateral direction as the sleeve 220 moves from the second position to return to the first position. The second lateral direction opposes the first lateral direction. The guide 380 is arranged to move the follower member second end 274 along a second path as the sleeve 220 moves from the second position to return to the first position.

At FIG. 11F the follower member has returned to the first position and is now held in the retaining section 292. The retaining section 292 is shaped to hold the follower member second end 274 within the retaining section 292 to resist movement of the sleeve 220 when the follower member second end 274 reaches the retaining section 292. The retaining section 292 includes an abutment surface 294 arranged to resist lateral movement of the follower member second end 274. Accordingly, the abutment surface 294 prevents the follower member second end 274 from returning to the initial lateral orientation 282 which prevents movement of the sleeve 220 after activation of the inhaler article 150.

After the inhaler article 150 is been removed from the sleeve 220, the follower member second end 274 moves out of contact with the guide, thus allowing movement of the sleeve 220. Furthermore, the follower member 270 returns to the initial lateral orientation 282 such that receiving an inhaler article, such as inhaler article 150, will place the lockout mechanism 390 in the arrangement depicted in FIG. 11A and the process can be repeated with additional inhaler articles.

In this example, the guide 380 comprises a protrusion. For instance, the guide 380 is formed on an inner surface of the holder 210, or the guide 380 is a separate component attached to the inner surface of the holder 210. In this example, the second end 274 of the follower member 270 comprises a tip engagement feature 377. As shown, the tip engagement feature 377 defines a quadrilateral shape. This shape may reduce the chance of the tip engagement feature catching on the surface of the guide 280 while facilitating being held in the retaining section 292. The second end 274 of the follower member 270 is arranged to contact the guide 380 when an inhaler article is received in the sleeve 220. The second end 274 is arranged to move along a perimeter of the guide 380 as the sleeve 220 is moved between the first and second positions while the second end 274 is in contact with the guide 380.

Figure 12C:
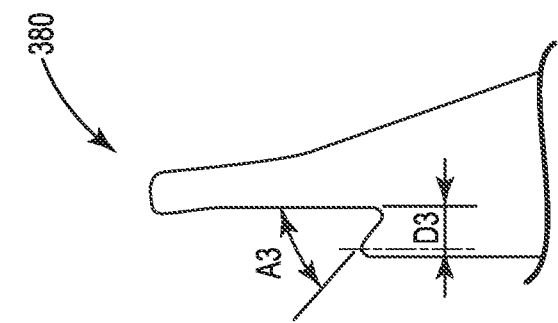
FIGS. 12A-12C are schematic diagrams of an illustrative guide.
Figure 12B:
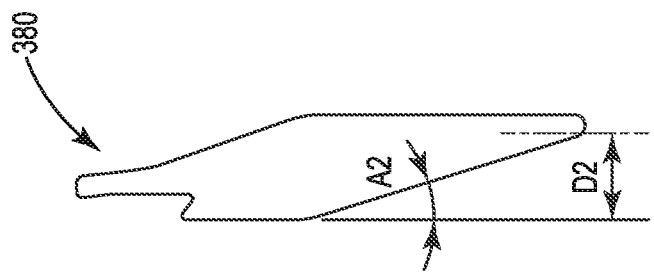
Figure 12A:
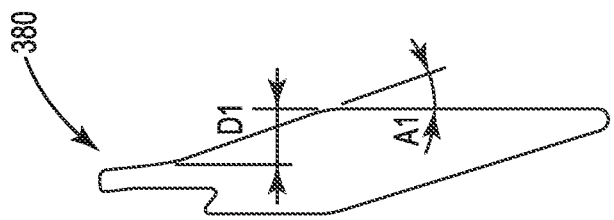

FIG. 12A is a schematic diagram of an illustrative guide 380 first, second, third and fourth portions, which may be referred to as "edges". The first portion is the first portion of the guide 380 with which the follower member 270 comes into contact when the follower member 270 first contacts the guide 380. The second portion is the portion of the guide 380 with which the follower member 270 comes into contact when the follower member 270 has left contact with the first portion of the guide 380. The third portion is the portion of the guide 380 with which the follower member 270 comes into contact when the follower member 270 has left contact with the second portion of the guide 380. The fourth portion is the portion of the guide 380 with which the follower member 270 comes into contact when the follower member 270 has left contact with the third portion of the guide 380, before coming into contact with the retaining section.

FIG. 12A shows a follower member tensioning rate angle A1 and a follower member tensioning rate distance D1. The tensioning rate angle A1 is the angle between the first and second portions of the guide 380. The follower member tensioning rate distance D1 is the lateral distance travelled by the follower member 270 along the first portion.

FIG. 12B is a schematic diagram of the illustrative guide 380 of FIG. 12A including follower member tensioning rate angle A2 and follower member tensioning rate distance D2. The tensioning rate angle A2 is the angle between the third and fourth portions of the guide 380. The follower member tensioning rate distance D2 is the lateral distance travelled by the follower member 270 along the third portion.

FIG. 12C is a schematic diagram of the illustrative guide 380 of FIGS. 12A and 12B including follower member tensioning rate angle A3 and follower member tensioning rate distance D3. The follower member tensioning rate angle A3 is the angle between the fourth portion and the retaining section surface. The follower member tensioning rate distance D3 is the lateral distance travelled by the follower member 270 along the retaining section surface.

The activation angle A1 is in a range of about 10 degrees to about 30 degrees. Preferably, the activation angle A1 is about 15 degrees. The activation distance D1 is in a range of about 0.5 millimetres to about 2 millimetres. Preferably, the activation distance D1 is about 1.2 millimetres.

The return angle A2 is in a range of about 10 degrees to about 30 degrees. Preferably, the return angle A2 is about 15 degrees. The return distance D2 is in a range of about 1 millimetres to about 3 millimetres. Preferably, the return distance D2 is about 1.7 millimetres.

The retainer angle A3 is in a range of about 10 degrees to about 90 degrees. Preferably, the retainer angle A3 is about 65-70 degrees. The retainer distance D3 is in a range of about 0.2 millimetres to about 1 millimetre. Preferably, the retainer distance D3 is about 0.45 millimetres.

Figure 13B:
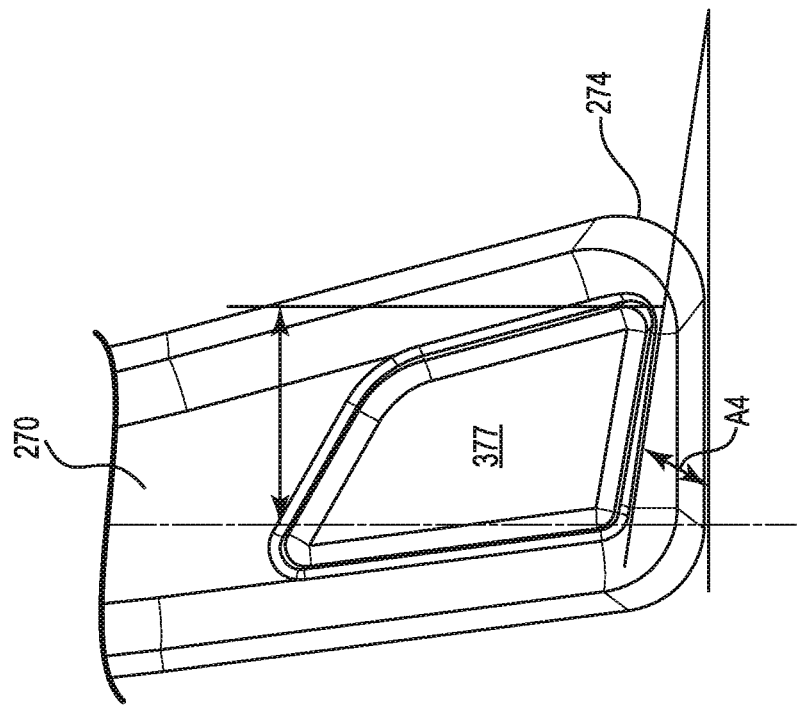
FIG. 13B is a perspective view of an illustrative follower member.
Figure 13A:
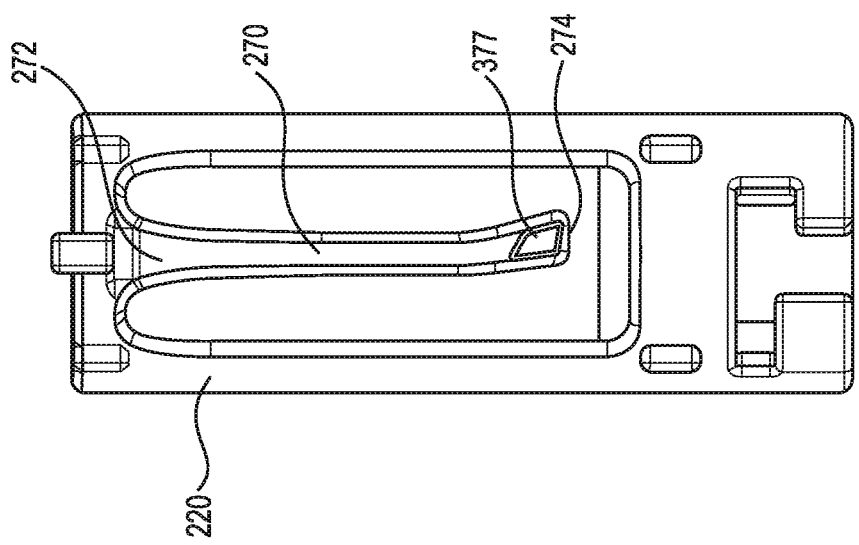

FIG. 13A is a cross-sectional schematic diagram of an illustrative sleeve 220. FIG. 13B is a perspective view of a second end 274 of the follower member 270 of FIG. 13A.

The follower member 270 extends between a first end 272 and a second end 274. The follower member 270 extends along a sleeve axis. The first end 272 may be coupled to or formed integrally with the sleeve 220. The second end 274 of the follower member 270 comprises a tip engagement feature 377. As shown, the tip engagement feature 377 has a quadralateral shape. The quadralateral shape has a major longitudinal axis 278. An engagement feature angle A4 is the angle at which the length of the engagement feature 277 is offset from an axis perpendicular to the length of the follower member 270 may be in a range of about 0 degrees to about 45 degrees. Preferably, the engagement feature angle A4 may be about 10 to 15 degrees.

The invention claimed is:

1. A holder for an inhaler article, the holder comprising:
   a sleeve positioned within a housing cavity, wherein the sleeve comprises a sleeve cavity arranged to receive the inhaler article and the sleeve is movable within the housing cavity between a first position and a second position;
   a piercing element arranged to pierce the inhaler article received within the sleeve when the sleeve is moved from the first position to the second position; and
   a lockout mechanism comprising a guide, a follower member coupled with the sleeve, and a retaining section;
   wherein the follower member is arranged to move along the guide into the retaining section as the sleeve moves from the second position and back to the first position; and
   wherein the retaining section is arranged to hold the follower member when the sleeve has returned back to the first position, thus retaining the sleeve in the first position, and the follower member is arranged to be in a neutral position in which the follower member does not interface with the guide when the inhaler article is not within the sleeve cavity.

2. The holder according to claim 1 wherein the follower member is movable relative to the sleeve, and the follower member is arranged to interface with the inhaler article when the inhaler article is inserted into the sleeve cavity so that the inhaler article moves the follower member out of the neutral position and into contact with the guide.

3. The holder according to claim 1 wherein the follower member extends within the sleeve cavity in the neutral position.

4. The holder according to claim 3 wherein the follower member is flexible so that the follower member deflects outwardly away from a longitudinal axis of the sleeve into contact with the guide when the inhaler article is received in the sleeve cavity.

5. The holder according to claim 1 wherein the follower member is biased towards the neutral position so that the follower member moves out of contact with the guide, or the retaining section when the inhaler article is removed from the sleeve.

6. The holder according to claim 1 wherein the guide is arranged to move the follower member in a first lateral direction away from an initial lateral orientation as the sleeve moves from the first position to the second position.

7. The holder according to claim 6 wherein the follower member is biased towards the initial lateral orientation; and
   wherein the guide is shaped so that the follower member returns to the initial lateral orientation when the sleeve is in the second position.

8. The holder according to claim 7 wherein the follower member and the guide are arranged to emit an audible sound when the follower member returns to the initial lateral orientation.

9. The holder according to claim 6 wherein the guide is arranged to move the follower member in a second lateral direction by the guide as the sleeve moves from the second position to return to the first position.

10. The holder according to claim 1 wherein the retaining section is shaped to hold the follower member within the retaining section to resist movement of the sleeve when the follower member reaches the retaining section.

11. The holder according to claim 1 wherein the follower member is an elongate member coupled with the sleeve.

12. The holder according to claim 11 wherein the elongate member is integrally formed with the sleeve.

13. The holder according to claim 1 wherein the guide comprises a protrusion.

14. The holder according to claim 1 wherein the guide comprises a channel.

* * * * *